(12) United States Patent
Burkhardt et al.

(10) Patent No.: US 6,384,013 B1
(45) Date of Patent: *May 7, 2002

(54) CYCLIC PEPTIDE ANTIFUNGAL AGENTS AND PROCESS FOR PREPARATION THEREOF

(75) Inventors: Frederick J. Burkhardt; Manuel Debono; Jeffrey S. Nissen, all of Indianapolis; William W. Turner, Jr., Bloomington, all of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/291,900

(22) Filed: Apr. 14, 1999

Related U.S. Application Data

(63) Continuation-in-part of application No. 08/449,056, filed on May 24, 1995, now Pat. No. 5,965,525, which is a division of application No. 08/032,228, filed on Mar. 17, 1993, now abandoned, which is a continuation-in-part of application No. 07/992,390, filed on Dec. 16, 1992, now abandoned, which is a continuation-in-part of application No. 07/854,117, filed on Mar. 19, 1992, now abandoned.

(51) Int. Cl.$^7$ .............................................. A61K 38/00

(52) U.S. Cl. ................................ 514/11; 514/2; 514/9; 530/317; 530/329

(58) Field of Search ................... 514/2, 9, 11; 530/329, 530/317

(56) References Cited

U.S. PATENT DOCUMENTS

| | | |
|---|---|---|
| 4,293,482 A | 10/1981 | Abbott et al. |
| 4,293,489 A | 10/1981 | Debono et al. ............. 590/317 |
| 4,304,716 A | 12/1981 | Abbott et al. |
| 4,927,831 A | 5/1990 | Malamas |
| 5,166,135 A | 11/1992 | Schmatz ....................... 514/11 |
| 5,376,634 A | 12/1994 | Iwamoto et al. |
| 5,541,160 A | 7/1996 | Balkovec et al. ............. 514/11 |
| 5,629,289 A | * 5/1997 | Rodriquez ................... 514/11 |
| 5,629,290 A | 5/1997 | LaGrandeur et al. ......... 514/11 |
| 5,646,111 A | 7/1997 | Borromeo et al. ............ 514/11 |
| 5,652,213 A | 7/1997 | Jamison et al. ............... 514/11 |
| 5,741,775 A | 4/1998 | Balkovec et al. ............. 514/11 |
| 5,786,325 A | 7/1998 | Borromeo et al. ............. 514/9 |

FOREIGN PATENT DOCUMENTS

| | | |
|---|---|---|
| DE | 2 803 581 | 8/1979 |
| EP | 359529 | 3/1990 |
| EP | 0 365 324 | 4/1990 |
| EP | 447186 | 9/1991 |
| EP | 448343 | 9/1991 |
| EP | 448353 | 9/1991 |
| EP | 448354 | 9/1991 |
| EP | 448355 | 9/1991 |
| EP | 448356 | 9/1991 |
| EP | 462531 | 12/1991 |
| EP | 486011 | 5/1992 |
| EP | 503960 | 9/1992 |
| EP | 525889 | 2/1993 |
| GB | 2241956 | 9/1991 |
| GB | 2242194 | 9/1991 |
| WO | WO 95/271074 | 10/1995 |

OTHER PUBLICATIONS

English Abstract for German Patent DE 2 803 581 retrieved in Dialog database in file 351 (Derwent) on Sep. 25, 2001.

* cited by examiner

*Primary Examiner*—Dwayne C. Jones
*Assistant Examiner*—C. Delacroix-Muirheid
(74) *Attorney, Agent, or Firm*—Morrison & Foerster LLP

(57) ABSTRACT

Provided are compounds of the formula (1):

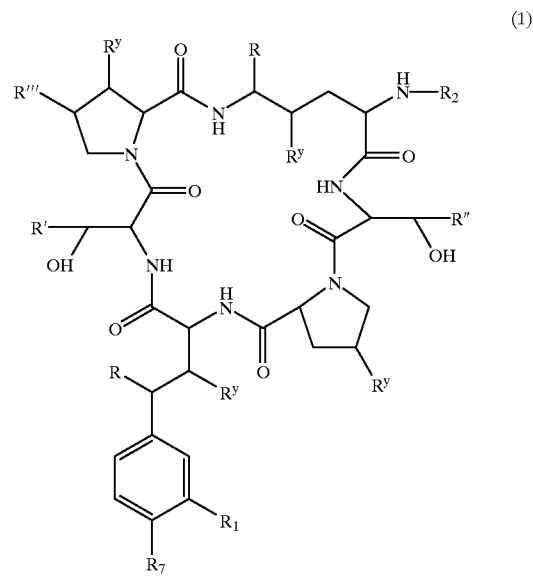

wherein

R' is hydrogen, methyl or $NH_2C(O)CH_2$—;

R" and R'" are independently methyl or hydrogen;

R and $R^y$ are independently hydroxy or hydrogen;

$R_1$ is hydroxy, hydrogen, or hydroxysulfonyloxy;

$R_7$ is hydroxy, hydrogen, hydroxysulfonyloxy or phosphonooxy;

$R_2$ is a acyl side chain. Also provided are formulations, methods of inhibiting fungal and parasitic activity, and a process for preparing dideoxy (R=H) forms of the compounds.

7 Claims, No Drawings

CYCLIC PEPTIDE ANTIFUNGAL AGENTS AND PROCESS FOR PREPARATION THEREOF

This application is a continuation of application Ser. No. 08/449,056 filed May 24, 1995, now U.S. Pat. No. 5,965,525, which is a division of application Ser. No. 08/032,228 filed Mar. 17, 1993, now abandoned, which is a continuation-in-part of application Ser. No. 07/992,390 filed Dec. 16, 1992, now abandoned, which is a continuation-in-part of application Ser. No. 07/854,117 filed Mar. 19, 1992, now abandoned.

BACKGROUND OF THE INVENTION

This invention relates to cyclic peptide antifungal agents. In particular, it relates to acyl derivatives of the echinocandin class of cyclic peptide antifungal agents; to methods for treating antifungal and parasitic infections, and to formulations useful in the methods.

The compounds provided by this invention are semi-synthetic antifungal agents in that they are derived from the cyclic peptide antifungals which are produced by culturing various microorganisms. A number of cyclic peptide antifungals are known. Among these are echinocandin B (A30912A), aculeacin, mulundocandin, sporiofungin, L-671,329, FR901379, and S31794/F1. All such antifungals are structurally characterized by a cyclic hexapeptide core, or nucleus, the amino group of one of the cyclic amino acids bearing a fatty acid acyl group forming a side chain off the core or nucleus. For example, echinocandin B has a linoleoyl side chain while aculeacin has a palmitoyl side chain. These fatty acid side chains of the cyclic hexa- peptides can be removed by enzymatic deacylation to provide the free nucleus. (Formula (1), hereinafter, wherein $R_2$ is hydrogen.) Reacylation of the amino group of the nucleus provides semi synthetic antifungal compounds. For example, the echinocandin B nucleus provides a number of antifungal agents when reacylated with certain unnatural side chain moieties (see Debono, U.S. Pat. No. 4,293,489). Among such antifungal compounds is cilofungin which is represented by the formula (1) wherein R is methyl, $R_1$ is hydrogen and $R_2$ is p-(n-octyloxy)benzoyl.

Enzymatic deacylation of the cyclic hexapeptides is carried out with deacylase produced by the organism *Actinoplanes utahensis* and related microorganisms as described by Abbott et al., U.S. Pat. No. 4,293,482.

The present invention provides acylated cyclic hexapeptides having unique side chain acyl groups which, inter alia impart enhanced antifungal and antiparasitic potency e.g. against pathogenic strains of *Candida albicans*. Also provided is a process for removing the aminal and benzylic hydroxy groups to result in a dideoxy compound of formula (1) (R=H).

SUMMARY OF THE INVENTION

The compounds provided by this invention are represented by the following formula (1):

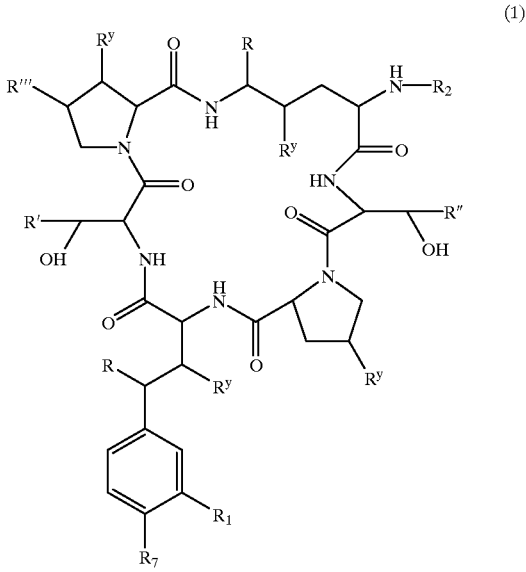

wherein
R' is hydrogen, methyl or $NH_2C(O)CH_2$—;
R" and R''' are independently methyl or hydrogen;
R and $R^y$ are independently hydroxy or hydrogen;
$R_1$ is hydroxy, hydrogen, or hydroxysulfonyloxy;
$R_7$ is hydroxy, hydrogen, hydroxysulfonyloxy or phosphonooxy; and I) $R_2$ is a substituted benzoyl group represented by the formula:

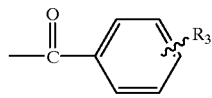

wherein
A) $R_3$ is a polyoxa-alkyl group represented by the formula

wherein m and n are integers of from 2 to 4, and p is 0 or 1; or

B) $R_3$ is an unsaturated hydrocarbon group represented by,the formula:

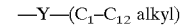

wherein Y is —C≡C— or —CH=CH—; or

C) $R_3$ is a group of the formula —O—$(CH_2)_m$—G, wherein m is as defined and G is $C_7$–$C_{10}$ bicycloalkyl or $C_7$–$C_{14}$ tricycloalkyl; or D) $R_3$ is quinolyl; or II) $R_2$ is an acyl group represented by the formula:

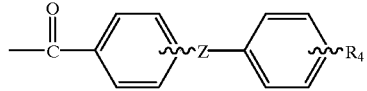

wherein
Z is —O—, —C≡C—, —CH=CH—, —$CH_2$—$CH_2$—, —$CH_2$—, or a carbon to carbon bond;

A) $R_4$ is hydrogen, $C_2$–$C_{12}$ alkynyl, $C_2$–$C_{12}$ substituted alkynyl, $C_3$–$C_{12}$ cycloalkyl, $C_7$–$C_{10}$ bicycloalkyl, $C_7$–$C_{14}$ tricycloalkyl, $C_1$–$C_{12}$ alkoxy, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halogen, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, phenyl substituted with a polyoxa-alkyl group represented by the formula:

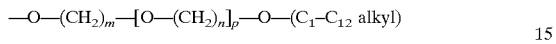

wherein m,n and p are as defined; or

C) $R_4$ is phenyl substituted with $C_1$–$C_6$ alkoxy substituted by fluoro, bromo, chloro or iodo; or D) $R_4$ is $C_1$–$C_{12}$ alkoxy substituted with $C_3$–$C_{12}$ cycloalkyl, $C_7$–$C_{10}$ bicycloalkyl, $C_7$–$C_{14}$ tricycloalkyl, $C_2$–$C_{12}$ alkynyl, amino, $C_1$–$C_4$ alkylamino, di-($C_1$–$C_4$ alkyl)amino, $C_1$–$C_{12}$ alkanoylamino, phenyl substituted with a polyoxa-alkyl group represented by the formula:

wherein m,n and p are as defined; or

E) $R_4$ is $C_1$–$C_{12}$ alkoxy substituted with a group of the formula:

wherein $R_8$ is $C_1$–$C_6$ alkoxy optionally substituted with phenyl; or

F) $R_4$ is a group represented by the formula:

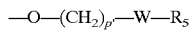

wherein p' is an integer of from 2 to 4; W is pyrrolidino, piperidino or piperazino, and $R_5$ is hydrogen, $C_1$–$C_{12}$ alkyl, $C_3$–$C_{12}$ cycloalkyl, benzyl or $C_3$–$C_{12}$ cycloalkylmethyl; or G) $R_4$ is a group represented by the formula:

wherein
Y has the same meanings defined above; and
$R_6$ is $C_1$–$C_{12}$ alkyl, $C_1$–$C_{12}$ substituted alkyl; $C_3$–$C_{12}$ cycloalkyl, $C_7$–$C_{10}$ bicycloalkyl, $C_7$–$C_{14}$ tricycloalkyl, phenyl, $C_3$–$C_{12}$ cycloalkenyl, naphthyl, benzothiazolyl, thienyl, indanyl, fluorenyl, phenyl substituted by amino, $C_1$–$C_{12}$ alkylthio, halogen, $C_1$–$C_{12}$ alkyl, $C_2$–$C_{12}$ alkenyl, $C_2$–$C_{12}$ alkynyl, $C_1$–$C_{12}$ alkoxy, trifluoromethyl, —O—($CH_2$)p'—W—$R_5$, or $C_1$–$C_6$ alkoxy substituted by fluoro, bromo, iodo or chloro; or
$R_6$ is a phenyl substituted by a polyoxa-alkyl group represented by the formula

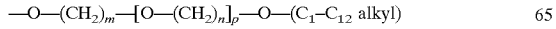

wherein m,n and p are as defined above; or

III) $R_2$ is a group having the formula:

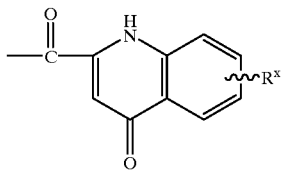

wherein $R^x$ is $C_1$–$C_{12}$ alkoxy or a polyoxa-alkyl group represented by the formula:

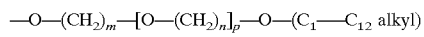

wherein m,n and p are as defined above; or

IV) $R_2$ is a group having the formula:

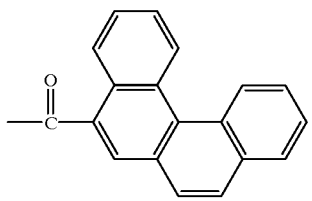

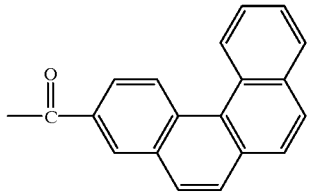

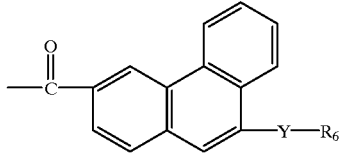

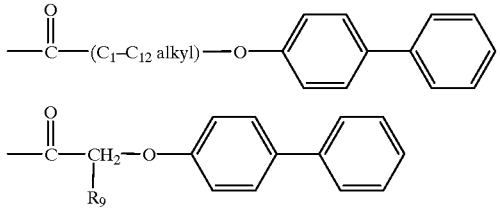

wherein $R_9$ is phenyl, $C_1$–$C_{12}$ alkyl, or $C_1$–$C_{12}$ alkoxy; or

V) $R_2$ is naphthoyl substituted with $R_4$; and the pharmaceutically acceptable non-toxic salts thereof;
with the proviso that when
R' is methyl or $NH_2C(O)CH_2$—;
R" is methyl;
R''' is methyl;
$R^Y$ is hydroxy;
R is hydroxy; and
either a) or b):
a) $R_1$ is hydroxysulfonyloxy and $R_7$ is hydroxy, hydroxysulfonyloxy or phosphonooxy;
b) $R_1$ is hydrogen or hydroxysulfonyloxy and $R_7$ is hydroxysulfonyloxy or phosphonooxy;

$R_2$ is not i)

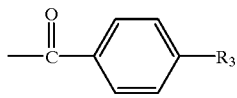

wherein $R_3$ is

—O—$(CH_2)_m$—[O—$(CH_2)_n$]$_p$—O—($C_1$-$C_{12}$ alkyl)

wherein p=0; nor ii)

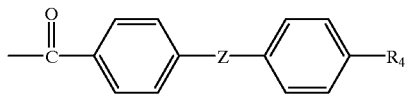

wherein Z is a carbon to carbon bond or —O— and $R_4$ is $C_1$-$C_{12}$ alkoxy; nor iii) naphthoyl substituted by $R_4$ wherein $R_4$ is hydrogen, phenyl, or $C_1$-$C_{12}$ alkoxy.

Also provided are formulations and methods for inhibiting parasitic and fungal activity which employ the compounds of the invention, and a process for preparing the dideoxy form of the compounds.

DETAILED DESCRIPTION

The term: "$C_1$-$C_{12}$ alkyl" refers to the straight or branched chain alkyl hydrocarbon groups such as, for example, methyl, ethyl, n-propyl, isopropyl, n-butyl, sec-butyl, t-butyl, pentyl, hexyl, heptyl, octyl, nonyl, decyl, undecyl and dodecyl groups; and the like.

The term "$C_2$-$C_{12}$ alkenyl" refers to groups such as vinyl, 1-propene-2-yl, 1-butene-4-yl, 1-pentene-5-yl, 1-butene-1-yl, and the like.

The term "$C_2$-$C_{12}$ alkynyl" refers to such groups as ethynyl, propynyl, pentynyl, butynyl and the like.

The term "$C_1$-$C_{12}$ alkylthio" refers to such groups as methylthio, ethylthio, t-butylthio, and the like.

The term "$C_1$-$C_{12}$ alkoxy" refers to the straight or branched chain oxyalkyl groups such as, e.g. methoxy, ethoxy, propoxy, butoxy, heptoxy, octyloxy, dodecyloxy, and the like.

The term "$C_3$-$C_{12}$ cycloalkoxy" refers to such groups as cyclopropoxy, cyclobutoxy and the like.

The term "$C_3$-$C_{12}$ cycloalkenyl" refers to such groups as cyclopropenyl, cyclobutenyl, cyclopentenyl, and the like.

The term "$C_1$-$C_{12}$ substituted alkyl," "$C_2$-$C_{12}$ substituted alkenyl", and "$C_2$-$C_{12}$ substituted alkynyl", denotes the above substituted one or two times with halogen, hydroxy, protected hydroxy, amino, protected amino, $C_1$-$C_7$ acyloxy, nitro, carboxy, protected carboxy, carbamoyl, carbamoyloxy, cyano, methylsulfonylamino, phenyl, substituted phenyl, or $C_1$-$C_{12}$ alkoxy.

The term "substituted phenyl" is represented by a phenyl group substituted with one, two, or three moieties chosen from halogen, hydroxy, protected hydroxy, cyano, nitro, $C_1$-$C_{12}$ alkyl, $C_1$-$C_{12}$ alkoxy, carboxy, protected carboxy, carboxymethyl, hydroxymethoyl, amino, aminomethyl trifluoromethyl or N-(methylsulfonylamino)

The term "$C_3$-$C_{12}$ cycloalkyl" refers to such groups as cyclopropyl, cyclobutyl, cyclopentyl, cyclohexyl and cycloheptyl.

The term "$C_1$-$C_4$ alkylamino" refers to such groups as methylamino, ethylamino, n-butylamino and the like.

The term "di-($C_1$-$C_4$ alkyl)amino" refers to such groups as dimethylamino, diethylamino, di-n-propylamino, di-n-butylamino, methylethylamino, methyl-n-butylamino, and like tertiary amino groups.

The term "$C_1$-$C_{12}$ alkanoylamino" refers to such groups as acylamino groups derived from the $C_1$-$C_{12}$ carboxylic acids and are exemplified by formamido, acetylamino, propionylamino, butyrylamino, and the like.

The term "$C_3$-$C_{12}$ cycloalkylmethyl" refers to those $C_3$-$C_7$ cycloalkyls,described above further substituted by methyl.

The terms "$C_7$-$C_{10}$ bicycloalkyl" and "$C_7$-$C_{14}$ tricycloalkyl" refer to such groups as bicyclo[2.2.1.]hept-2-yl, bicyclo[2.2.1.]hep-4-en-2-yl, bicyclo[3.3.1.]nona-3-yl, bicyclo[3.3.1.]nona-2-yl, bicyclo[3.2.1.]oct-2-yl, bicyclo[2.2.2.]oct-2-yl, bicyclo[2.2.2]oct-5-en-2-yl, adamantyl and the like.

The term "dideoxy" refers to compounds of the formula (1) wherein R=H.

The term "inhibiting", such as used in relation to the methods for inhibiting parasitic and fungal activity, is defined to mean its normal definition, i.e., to stop, retard or prophylactically hinder or prevent.

The term "activity", as used in relation to parasitic and fungal activity, includes growth thereof and attending characteristics and results from the existence of the parasite or fungus.

The term "contacting", as used in relation to the methods for inhibiting parasitic and fungal activity by contacting a compound of the invention with a parasite or fungus, is defined to mean its normal definition. However, the term does not imply any further limitations to the process, such as by mechanism of inhibition, and the methods are defined to encompass the spirit of the invention, which is to inhibit parasitic and fungal activity by the action of the compounds and their inherent anti-parasitic and anti-fungal properties, or in other words, the compounds, used in the method are the causative agent for such inhibition.

Examples of acyl groups represented by $R_2$ in formula (1) are benzoyl substituted by polyoxa-alkyl groups such as, e.g., 2-methoxyethoxy (p=0, m=1), 2-ethoxyethoxy, 2-(2-ethoxyethoxy)ethoxy (m=2, p=1, n=2), 3-(2-ethoxyethoxy)-propoxy, 3-(2-methoxyethoxy)butoxy, and like groups.

Examples of $R_3$ groups wherein $R_2$ is benzoyl substituted by an unsaturated hydrocarbon groups —Y—($C_1$-$C_{12}$-alkyl) include e.g., acetylenic groups —C≡C—($C_1$-$C_{12}$ alkyl) and —$CH_2$=$CH_2$—($C_1$-$C_{12}$ alkyl) which may be cis- or trans- e.g. propenyl, butenyl, hexenyl, decenyl, and the like; propynyl, butynyl, hexynyl, undecynyl, and like alkynes.

Examples of acyl groups wherein $R_2$ is a group represented by the formula:

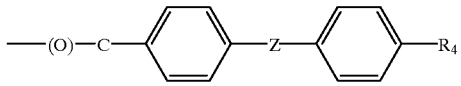

are diphenyl ethers (Z=—O—), diphenyl acetylenes (Z=—C≡C—), stilbenes (Z=—CH=CH—), and biphenyls (Z=a carbon to carbon bond). Among examples of such biphenyl groups, wherein Z is a carbon to carbon bond i.e. a phenyl to phenyl bond, are 4-[4-(butyloxy)phenyl]

benzoyl, 4-[4-(cyclobutylmethoxy)-phenyl]benzoyl, 4-[4-cyclopentyl-methoxy)phenyl]benzoyl, 4-[4-(cyclohexylethoxy)-phenyl]benzoyl, 4-[4-(n-hexyloxy)-phenyl]benzoyl, 4-phenylbenzoyl, 4-[4-(11-amino-undecyloxy)-phenyl]benzoyl, 4-[4-(11-formamidoundecyloxy)phenyl]benzoyl, 4-[4-(iso-pentyloxy)phenyl]benzoyl, and the like. Examples of such diphenyl ether acyl groups $R_2$ of the formula above wherein Z is an oxygen atom are 4-(4-butyloxyphenoxy)benzoyl, 4-(4-hexyloxyphenoxy)benzoyl, 4-(4-ethoxyphenoxy) benzoyl, 4-(4-benzyloxyphenoxy)benzoyl, 4-[4-(3-chlorobutyloxy)phenoxy]benzoyl, 4-(4-4decyloxyphenoxy) benzoyl, 4-[4-(3-di-methylaminopropoxy)phenoxy]benzoyl and the like. Examples of diphenylacetylene and stilbene acyl groups, $R_2$, wherein Z is an acetylenic bond or an ethylene bond are 4-styrylbenzoyl, 4-(4-methoxystyryl) benzoyl, 4-(4-butyloxystyryl)benzoyl, 4-(phenylethynyl) benzoyl, 4-(4-ethoxyphenylethynyl)benzoyl, 4-(4-cyclohexyloxyphenyl-ethynyl)benzoyl, and the like. Examples of $R_2$ acyl groups represented by the foregoing formula wherein Z is a carbon to carbon bond and $R_4$ is represented by the formula —O—$(CH_2)_{p'}$—W—$R_5$ are 4-[4-[2-(N-cyclohexylpiperidine-4-yl)ethoxy]phenyl] benzoyl, 4-[4-[2-(N-hexylpiperidine-4-yl)ethoxy]phenyl] benzoyl, 4-[4-[2-(4-benzylpiperidino)ethoxy]phenyl] benzoyl, 4-[4-[2-(4-cyclohexylpiperidino)ethoxy]phenyl] benzoyl and like diphenyl acyl groups. Examples of such acyl groups wherein $R_4$ is represented by the formula —Y—$R_6$ include 4-[4-(phenylethynyl)phenyl]benzoyl, 4-[4-(phenylethynyl)phenoxy]benzoyl, 4-[4-(hexynyl) phenyl]benzoyl, 4-[4-(styryl)phenoxy]benzoyl, 4-[4-4-benzylphenylethynyl)-phenyl]benzoyl, 4-[4-[4-[4-methylpiperidino)ethoxy]phenylethynyl]phenyl]benzoyl and like acyl groups. Such acyl groups wherein $R_4$ is represented by the formula —O—$(CH_2)_{p'}$—W—$R_5$ form salts of the basic amino groups of the piperidine and piperazine heterocyclic groups with both organic and inorganic acids such as hydrochloric acid, hydrobromic acid, sulfuric acid and phosphoric acid and with organic acids such as the sulfonic acids, benzenesulfonic acid, toluene-sulfonic acid, methanesulfonic acid, acetic acid, chloroacetic acid, trifluoroacetic acid, benzoic acid, isophthalic acid, salicylic acid, citric acid, malic acid, succinic acid, malonic acid and like acids.

The following tables contain further examples of the cyclic peptides represented by the formula (1). Table 1 contains examples of cyclic peptides wherein the acyl group $R_2$ is of the formula:

TABLE 1

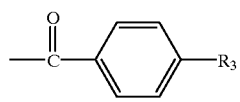

$R_2$

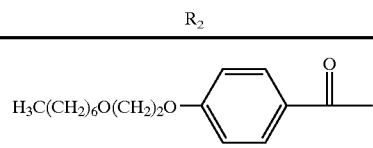

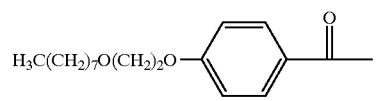

TABLE 1-continued

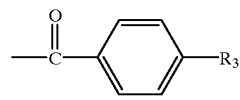

$R_2$

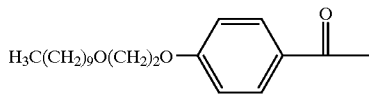

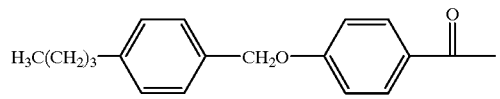

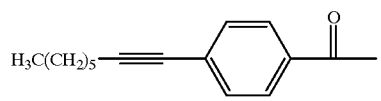

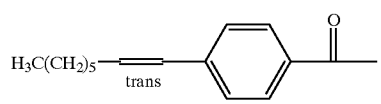

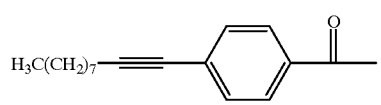

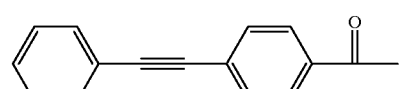

The following Table 2 illustrates the compound of the formula (1) wherein $R_2$ is represented by the formula:

TABLE 2

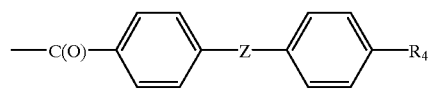

$R_2$

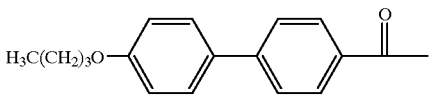

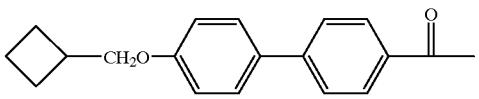

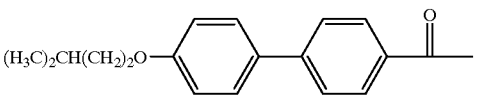

TABLE 2-continued

| —C(O)—⟨Ph⟩—Z—⟨Ph⟩—R₄ |
|---|
| R₂ |

H₃C(CH₂)₄O(CH₂)₂O—

CH₃(CH₂)₄O— cyclopentyl-CH₂O—

(CH₃)₃C(CH₂)₂O—

(H₃CCH₂)₂CHCH₂O—

CH₃(CH₂)₅O— cyclohexyl-(CH₂)₂O—

Ph-C≡C—

H₃C(CH₂)₃-C≡C—

H₃C(CH₂)₃O—⟨Ph⟩—O—

H₃C(CH₂)₅O—⟨Ph⟩—O—

Ph—⟨Ph⟩—

TABLE 2-continued

| —C(O)—⟨Ph⟩—Z—⟨Ph⟩—R₄ |
|---|
| R₂ |

Ph-CH₂OC(O)NH(CH₂)₁₁O—

NH₂(CH₂)₁₁O—

HC(O)—NH(CH₂)₁₁O—

The following Table 3 illustrates compounds of formula 1 wherein R₂ is of the formula as indicated from Table 2 and R₄ is represented by the formula: —O—(CH₂)p-W—R₅.

TABLE 3

| R₂ |
|---|

H₃C(CH₂)₂-piperidinyl-(CH₂)₂O—

Ph-CH₂-piperidinyl-(CH₂)₂O—

H₃C(CH₂)₅N-piperidinyl-(CH₂)₂O— cyclohexyl-CH₂N-piperidinyl-(CH₂)₂O— cyclohexyl-piperidinyl-(CH₂)₂O— cyclohexyl-CH₂-cyclohexyl-(CH₂)₂O—

H₃C(CH₂)₅-piperidinyl-(CH₂)₃O—

TABLE 3-continued $R_2$

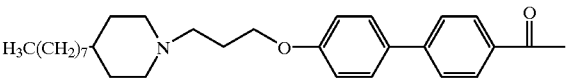

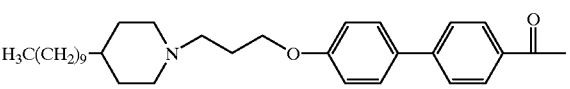

The acyl cyclohexapeptides represented by formula (1) exhibit antiparasitic activity, for example, they are especially active against the infectious fungi *Candida albicans* and *Candida parasilosis*. They also exhibit significant activity against *Aspergillus fumigatus*. They are active both in vitro and in vivo and accordingly are useful in combating systemic fungal infections.

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia in AIDS sufferers.

The antifungal activity of the compounds of the invention is determined in vitro in standard agar dilution tests and disc-diffusion tests wherein minimum inhibitory concentrations of the test compounds obtained. Standard in vivo tests in mice are used to determine the effective dose of the test compounds in controlling systemic fungal infections.

Tables 4A–E below contain the minimum inhibitory concentrations (MIC) in micrograms per milliliter (mcg/ml) for compounds of the invention against *Candida albicans* and *Candida parapsilosis,* and for certain compounds, the effective dose, $ED_{50}$, in mice.

In Tables 4A–E, $R'=CH_3$, $R''=CH_3$, $R'''=CH_3$, $R^y=OH$, $R_7=OH$ and $R_1=H$, In Tables 4A–D, $R=OH$, while in Table E, $R=H$.

In the Table 4A, $R_2$ is of the formula:

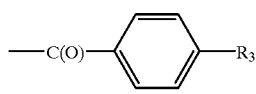

with $R_3$ being as indicated in the Table 4.
In Table 4B, $R_2$ is of the formula:

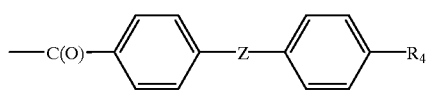

where Z is —O— and $R_4$ is as indicated.
Table 4C is as Table 4B, except Z is a carbon-carbon bond.
Table 4D indicates compound activities in which $R_2$ is as defined.
In Table 4E, dideoxy (where R=H) compounds are illustrated with $R_2$ as indicated.

TABLE 4A

| $R_3$ | MIC (mcg/ml) | | $ED_{50}$ (mg/kg) |
|---|---|---|---|
| | C. alb. | C. parap. | |
| —O(CH$_2$)$_2$—O—(CH$_2$)$_2$—O—C$_2$H$_5$ | >20 | 40 | — |
| —O—(CH$_2$)$_2$—O—C$_5$H$_{11}$ | >20 | 40 | — |
| —O—(CH$_2$)$_2$—OC$_7$H$_{15}$ | 10 | 40 | 30.3 |
| —O—(CH$_2$)$_2$—O—C$_8$H$_{17}$ | 2.5 | 80 | 4.4 |
| —O—(CH$_2$)$_2$—O—C$_{10}$H$_{21}$ | 0.625 | 5 | 9.5 |
| —C≡C—C$_5$H$_{11}$ | 2.5 | 29 | 10.5 |
| —CH=CH—C$_6$H$_{13\ (trans)}$ | 0.312 | 20 | 4.4 |
| —C≡C—C$_8$H$_{17}$ | 0.156 | 10 | — |

TABLE 4B

| $R_4$ | MIC (mcg/ml) | | $ED_{50}$ (mg/kg) |
|---|---|---|---|
| | C.alb | C.parap. | |
| —O—C$_4$H$_9$ | >20 | 40 | — |
| —O—C$_6$H$_{13}$ | 1.25 | >20 | 22.9 |

TABLE 4C

| $R_4$ | MIC (mcg/ml) | | $ED_{50}$ (mg/ml) |
|---|---|---|---|
| | C. alb. | C. parap. | |
| —O—C$_4$H$_9$ | 0.78 | 10 | 0.84 |
| —O—CH$_2$-cyclobutyl | 0.312 | 10 | 2.50 |
| —O—CH$_2$-cyclopentyl | 0.039 | 2.5 | 1.20 |
| —O—C$_5$H$_{11}$ | 0.156 | 0.625 | 1.86 |
| —O—C$_6$H$_{13}$ | 0.039 | 1.25 | 1.10 |
| —O—CH$_2$CH$_2$-cyclohexyl | 0.039 | 20 | 1.6 |
| —O—CH$_2$—CH(C$_2$H$_5$)—C$_2$H$_5$ | 0.039 | 2.5 | 4.6 |
| —O—CH$_2$—CH$_2$—CH(CH$_3$)$_2$ | 0.309 | 5 | 2.00 |
| —O—CH$_2$—CH$_2$—C(CH$_3$)$_3$ | 0.039 | 2.5 | 2.21 |
| —O—(CH$_2$)$_2$—O—C$_5$H$_{11}$ | 1.25 | 20 | 0.60 |
| —C≡C—C$_4$H$_9$ | 0.039 | 2.5 | 1.20 |
| —C≡C—C$_6$H$_5$ | 0.039 | 0.625 | 0.60 |
| —C$_6$H$_5$ | 0.078 | 10 | 1.3 |
| —O—(CH$_2$)$_2$—N(CH$_3$)$_2$ | >20 | >20 | — |
| —O—(CH$_2$)$_2$—N⟨piperidinyl⟩ | >20 | >20 | — |
| —O—(CH$_2$)$_2$—N⟨piperidinyl-C$_3$H$_7$⟩ | 5 | >20 | 3.0 |
| —O—(CH$_2$)$_2$—N⟨piperidinyl-cyclohexyl⟩ | 0.312 | 40 | 0.64 |
| —O—(CH$_2$)$_2$—N⟨piperidinyl-CH$_2$C$_6$H$_{11}$⟩ | 0.039 | 5 | 0.24 |

TABLE 4D
| R₂ | MIC (mcg/ml) | |
|---|---|---|
| | C. alb. | C. parap. |
| 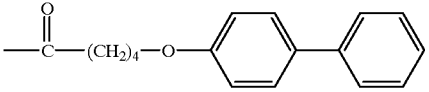 | 40 | >80 |
| 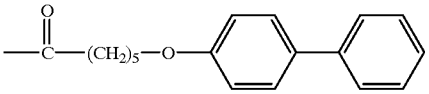 | 1.25 | 80 |
| 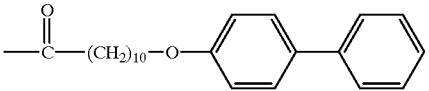 | 0.0039 | 2.5 |
| 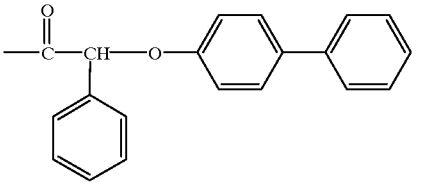 | 5 | >80 |
| 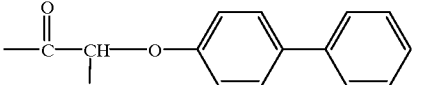 | 80 | >80 |
| 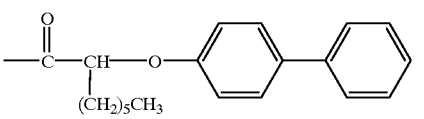 | 80 | >80 |
| 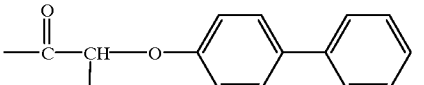 | 10 | >80 |
| 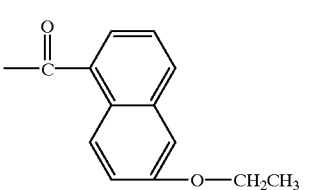 | >80 | >80 |
| 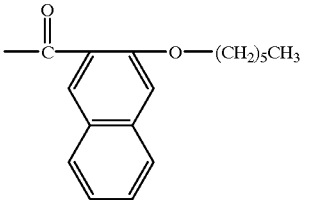 | 20 | >80 |

TABLE 4D-continued
| R₂ | MIC (mcg/ml) | |
|---|---|---|
|  | C. alb. | C. parap. |
| 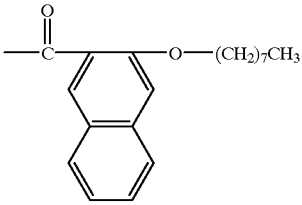 | 10 | >80 |
| 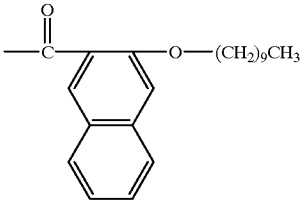 | 20 | >80 |
| 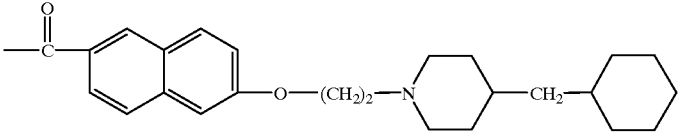 | 20 | >80 |
| 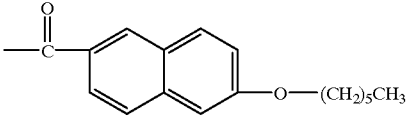 | 0.039 | 5 |
| 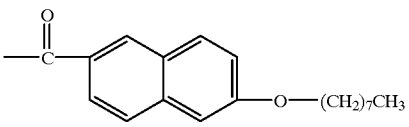 | 0.078 | 0.312 |
| 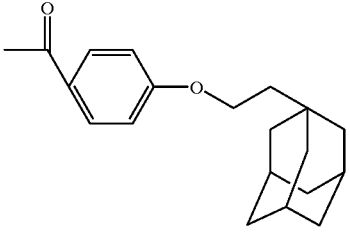 | 0.5 | 80 |
| 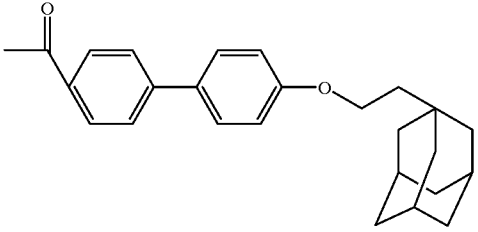 | 0.005 | 0.156 |

TABLE 4D-continued

| R₂ | MIC (mcg/ml) C. alb. | MIC (mcg/ml) C. parap. |
|---|---|---|
| [acetyl-naphthyl-O-CH₂CH₂-adamantyl] | 0.039 | 0.156 |
| —C(O)—(CH₂)₇—O—C₆H₄—C₆H₅ | 0.156 | 20 |
| [acetyl-naphthyl-O—(CH₂)₉CH₃] | 0.005 | 0.312 |
| [acetyl-naphthyl-C≡C-phenyl] | 0.312 | 5 |
| [acetyl-naphthyl-O-CH₂-biphenyl] | 0.312 | >80 |
| [acetyl-naphthyl-O-CH₂-naphthyl] | 0.078 | >20 |

TABLE 4E

| R₂ | MIC (mcg/ml) C. alb. | MIC (mcg/ml) C. parap. |
|---|---|---|
| —C(O)—C₆H₄—C₆H₄—O—C₄H₉ | 0.039 | 5.0 |
| —C(O)—C₆H₄—C₆H₄—O—C₅H₁₁ | >20 | 1.25 |

TABLE 4E-continued
| R$_2$ | MIC (mcg/ml) | |
|---|---|---|
| | C. alb. | C. parap. |
| 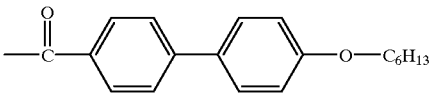 | 0.039 | 2.5 |
| 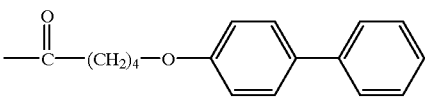 | >80 | >80 |
| 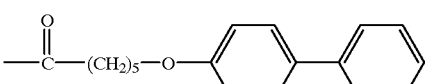 | 1.25 | 40 |
| 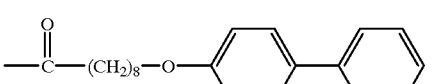 | 0.005 | 2.5 |
| 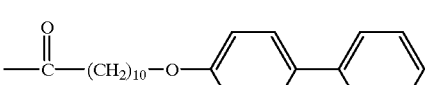 | 0.0098 | 0.625 |
| 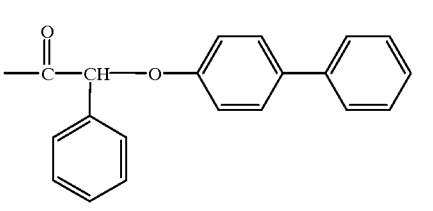 | 80 | >80 |
| 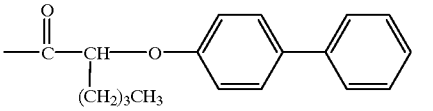 | 20 | >80 |
| 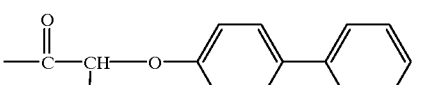 | 40 | >80 |
| 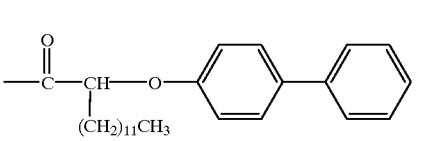 | 1.25 | >80 |
| 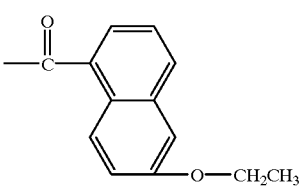 | >80 | >80 |

TABLE 4E-continued
| R₂ | MIC (mcg/ml) | |
|---|---|---|
| | C. alb. | C. parap. |
| 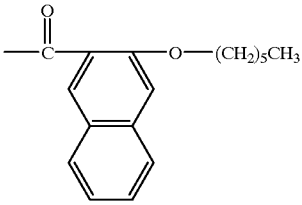 | 10 | >80 |
| 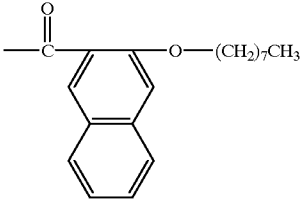 | 10 | >80 |
| 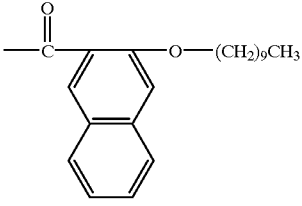 | 5.0 | >80 |
| 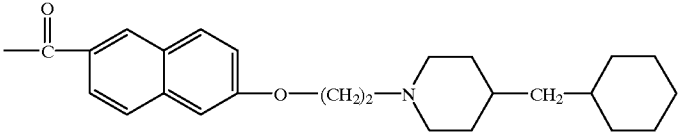 | 1.25 | >80 |
| 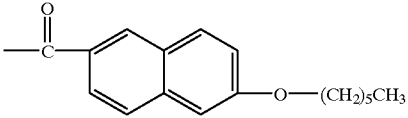 | 0.078 | 1.25 |
| 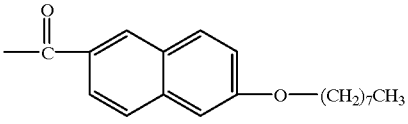 | 0.039 | 0.125 |
| 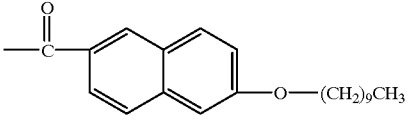 | 0.156 | 0.625 |
| 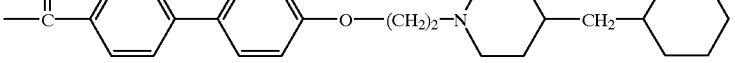 | 0.156 | 5.0 |

TABLE 4E-continued

| R$_2$ | MIC (mcg/ml) | |
| --- | --- | --- |
| | C. alb. | C. parap. |
| (4-(2-adamantylethoxy)phenyl carbonyl) | 0.625 | 80 |
| (4'-(2-adamantylethoxy)biphenyl-4-carbonyl) | 0.005 | 0.156 |
| (6-(2-adamantylethoxy)naphthalen-2-carbonyl) | 0.039 | 0.156 |

The non-dideoxy compounds of the invention (formula (1) are prepared with the amino nuclei of the cyclic hexapeptides which are represented by the formula when R$_2$ is hydrogen. These amino nuclei are obtained from the known natural products by the known enzymatic deacylation by which the fatty acid side chains of the natural compounds are removed. For example, echinocandin B which can be represented by the formula (1) wherein R'=R"=R'"=methyl, R is OH, R$^y$ is hydroxy, R$_1$ is H, R$_7$ is OH, and R$_2$ is linoleoyl, is deacylated to provide the echinocandin B nucleus (R$_2$=H) with the deacylase produced by the organism Actinoplanes utahensis as described by U.S. Pat. Nos. 4,293,482 and 4,304,716.

The known natural cyclic hexapeptides which are N-deacylated to provide the amino nuclei starting materials include echinocandin B (also known as A-30912A), aculeacin (palmitoyl side chain), tetrahydoechinocandin B (stearoyl side chain), mulundocandin (branched C$_{15}$ side chain), L-671,329 (C$_{16}$ branched side chain), S 31794/F1 (tetradecanoyl side chain), sporiofungin (C$_{15}$ branched side chain) and FR901379 (palmitoyl side chain). The amino nuclei obtained by the N-deacylation are then acylated by employing known amino acylation procedures to provide the N-acyl cyclic hexapeptides represented by the formula (1) wherein R$_2$ represents the acyl groups defined hereinabove. The acylating moiety is preferably an active ester of the carboxylic acid RCOOH such as the 2,4,5-trichlorophenyl ester. The R$_2$COOH precursor acids are prepared by the hydrolysis of the nitrile R$_2$CN or the ester R$_2$COOC$_1$–C$_4$ alk. These nitrile and ester intermediates are prepared by known methods.

The alkoxy aromatic (ie. phenyl and biphenyl) compounds of Tables 5–10 are prepared by one of the two following procedures:

A. The hydroxyaromatic compound (1 equivalent) is dissolved in acetonitrile (200–300 ml) and a base, such as potassium t-butoxide or potassium carbonate,(1-equivalent), is added. An alkyl bromide, iodide, or p-toluenesulfonate (1 equivalent) is then added and the solution is refluxed for 6 hours. The solvent is evaporated in vacuo and the residue is dissolved in ether and 2N sodium hydroxide. The ether layer is dried over magnesium sulfate and evaporated to give the alkoxyaromatic product.

B. The hydroxyaromatic compound (1 equivalent), alkyl alcohol (1 equivalent), and triphenylphosphine (1 equivalent) are dissolved in tetrahydrofuran (200–300 ml) and diethylazodicarboxylate (1 equivalent) is added dropwise over 10 minutes at room temperature. After 17 hours the solvent is removed in vacuo and the residue is dissolved in ether. This organic layer is extracted with 2N sodium hydroxide solution, dried over magnesium sulfate, and evaporated to give a product which is crystallized from ether/pentane or, if the product contains a tertiary amine, the hydrochloride salt is formed and crystallized from methanol/ethyl acetate.

TABLE 5

| Alkyl halide or tosylate | Wt. g | Method | R₁ | R₂ | Wt. g |
|---|---|---|---|---|---|
| I(CH₂)₃CH₃ | 9.4 | A | —(CH₂)₃CH₃ | CN | 3.2 |
| CH₃-C₆H₄-SO₃—CH₂-cyclobutyl | 12.3 | A | CH₂-cyclobutyl | CN | 5.3 |
| Br(CH₂)₂CH(CH₃)₂ | 7.7 | A | —(CH₂)₂CH(CH₃)₂ | CN | 9.2 |
| CH₃-C₆H₄-SO₃—(CH₂)₂O(CH₂)₄CH₃ | 7.6 | A | (CH₂)₂O(CH₂)₄CH₃ | CN | 4.8 |
| Br(CH₂)₄CH₃ | 15.3 | A | —(CH₂)₄CH₃ | CN | 20.3 |
| CH₃-C₆H₄-SO₃—CH₂-cyclopentyl | 13.0 | A | CH₂-cyclopentyl | CN | 12.2 |
| CH₃-C₆H₄-SO₃—(CH₂)₂C(CH₃)₃ | 13.1 | A | (CH₂)₂C(CH₃)₃ | CN | 11.8 |
| BrCH₂CH(CH₂CH₃)₂ | 8.5 | A | —CH₂CH(CH₂CH₃)₂ | CN | 3.0 |
| I(CH₂)₅CH₃ | 10.8 | A | —(CH₂)₅CH₃ | CN | 11.4 |
| Br(CH₂)₂-cyclohexyl | 4.2 | A | (CH₂)₂-cyclohexyl | CO₂CH₃ | 4.5 |

TABLE 6

| Alcohol | wt. g | Method | R | wt. g |
|---|---|---|---|---|
| HO(CH₂)₂—N(piperidine)—(CH₂)₂CH₃ | 3.6 | B | (CH₂)₂—N(piperidine)—(CH₂)₂CH₃ | 6.2 |
| HO(CH₂)₂—N(piperidine)—CH₂-C₆H₅ | 6.1 | B | (CH₂)₂—N(piperidine)—CH₂-C₆H₅ | 4.3 |
| HO(CH₂)₂-piperidine-N(CH₂)₅CH₃ | 0.5 | B | (CH₂)₂-piperidine-N(CH₂)₅CH₃ | 0.8 |
| HO(CH₂)₂-piperidine-NCH₂-cyclohexyl | 0.5 | B | (CH₂)₂-piperidine-NCH₂-cyclohexyl | 0.5 |
| HO(CH₂)₂—N(piperidine)-cyclohexyl | 2.3 | B | (CH₂)₂—N(piperidine)-cyclohexyl | 1.3 |

TABLE 6-continued

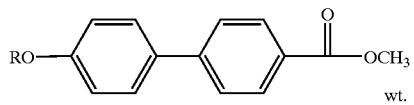

| Alcohol | wt. g | Method | R | wt. g |
|---|---|---|---|---|
| HO(CH$_2$)$_2$–N-piperidine–CH$_2$–cyclohexyl | 9.3 | B | (CH$_2$)$_2$–N-piperidine–CH$_2$–cyclohexyl | 9.6 |

TABLE 7

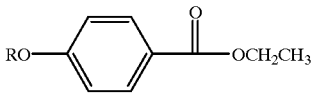

| Tosylate or alcohol | wt. g | Method | R | wt. g |
|---|---|---|---|---|
| CH$_3$–C$_6$H$_4$–SO$_3$–(CH$_2$)$_2$O(CH$_2$)$_6$CH$_3$ | 23.4 | A | —(CH$_2$)$_2$O(CH$_2$)$_6$CH$_3$ | 20.9 |
| CH$_3$–C$_6$H$_4$–SO$_3$–(CH$_2$)$_2$O(CH$_2$)$_7$CH$_3$ | 25.8 | A | —(CH$_2$)$_2$O(CH$_2$)$_7$CH$_3$ | 7.9 |
| CH$_3$–C$_6$H$_4$–SO$_3$–(CH$_2$)$_2$O(CH$_2$)$_9$CH$_3$ | 27.1 | A | —(CH$_2$)$_2$O(CH$_2$)$_9$CH$_3$ | 21.0 |
| HOCH$_2$–C$_6$H$_4$–(CH$_2$)$_3$CH$_3$ | 10.0 | B | CH$_3$–C$_6$H$_4$–(CH$_2$)$_3$CH$_3$ | 13.6 |

TABLE 8

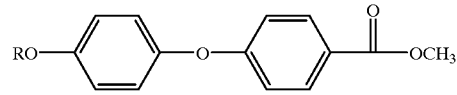

| Alkyl halide | wt. g | Method | R | wt. g |
|---|---|---|---|---|
| I(CH$_2$)$_3$CH$_3$ | 6.1 | A | —(CH$_2$)$_3$CH$_3$ | 12.3 |
| I(CH$_2$)$_5$CH$_3$ | 4.3 | A | —(CH$_2$)$_5$CH$_3$ | 4.7 |

TABLE 9

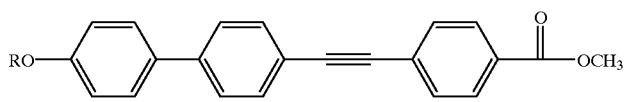

| Alkylhalide or tosylate | Wt. g | Method | R | Wt. g |
|---|---|---|---|---|
| I(CH$_2$)$_2$CH$_3$ | 2.6 | A | —(CH$_2$)$_2$CH$_3$ | 4.4 |
| H$_3$C–C$_6$H$_4$–SO$_3$–(CH$_2$)$_2$O(CH$_2$)$_3$CH$_3$ | 2.7 | A | —(CH$_2$)$_2$O(CH$_2$)$_3$CH$_3$ | 2.6 |

TABLE 9-continued

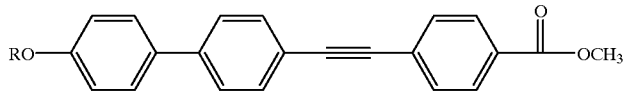

| Alkylhalide or tosylate | Wt. g | Method | R | Wt. g |
|---|---|---|---|---|
| 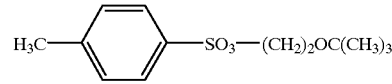 | 2.7 | A | —(CH$_2$)$_2$OC(CH$_3$)$_3$ | 2.6 |

TABLE 10

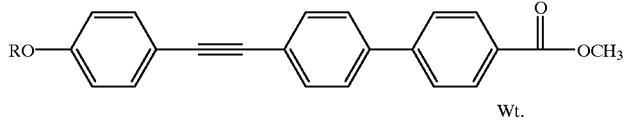

| Alkylhalide or tosylate | Wt. g | Method | R | Wt. g |
|---|---|---|---|---|
| I(CH$_2$)$_2$CH$_3$ | 3.8 | A | —(CH$_2$)$_2$CH$_3$ | 1.4 |
| 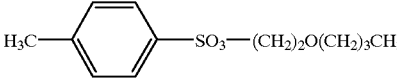 | 3.6 | A | —(CH$_2$)$_2$O(CH$_2$)$_3$CH$_3$ | 5.1 |
| 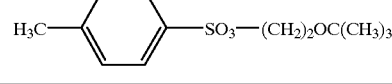 | 4.9 | A | —(CH$_2$)$_2$OC(CH$_3$)$_3$ | 5.2 |

The alkynyl and alkenyl aromatic compounds contained in Tables 11–14 are prepared by the following procedure:

An aromatic bromide, iodide, or trifluoromethanesulfonate (1 equivalent) is dissolved in acetonitrile (600 ml/0.1 mole of aromatic reactant) under a nitrogen atmosphere. An alkyne or alkene (1 equivalent), triethylamine (2 equivalents), palladium dichloride (0.05 equivalents), triphenylphosphine (0.1 equivalents), and cuprous iodide (0.025 equivalents) are added and the solution is refluxed for 17 hours. The solvent is removed in vacuo and the residue is slurried in ether (300 ml). Solids are removed by filtration and the filtrate is washed with 1N hydrochloric acid solution. The organic layer is dried over magnesium sulfate and evaporated to yield the product.

TABLE 11

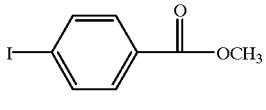

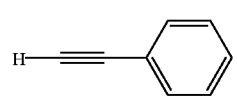

| Acetylene or olefin | wt. g | wt. g | R | wt. g |
|---|---|---|---|---|
| H—≡—(CH$_2$)$_5$CH$_3$ | 12.1 | 28.8 | —C≡—(CH$_2$)$_5$CH$_3$ | 26.2 |
| H—≡—(CH$_2$)$_5$CH$_3$ | 6.1 | 14.4 | —CH═—(CH$_2$)$_5$CH$_3$ (trans) | 0.6 |
| H—≡—(CH$_2$)$_7$CH$_3$ | 15.2 | 28.8 | —C≡—(CH$_2$)$_7$CH$_3$ | 28.2 |
| 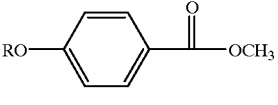 | 1.9 | 5.1 | 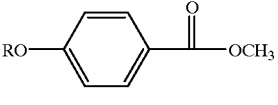 | 1.9 |
| H—≡—Si(CH$_3$)$_3$ | 4.3 | 11.5 | —≡—Si(CH$_3$)$_3$ | 11.2 |

TABLE 12
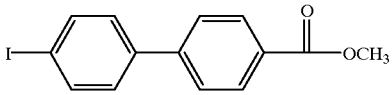
| Acetylene | wt. g | wt. g | R | wt. g |
|---|---|---|---|---|
| H—≡—C₆H₅ | 1.8 | 6.0 | —C≡—C₆H₅ | 2.6 |
| H—≡—(CH₂)₃CH₃ | 1.4 | 6.0 | —C≡—(CH₂)₃CH₃ | 5.1 |
| H—≡—Si(CH₃)₃ | 10.9 | 40.0 | —≡—Si(CH₃)₃ | 23.3 |
TABLE 13
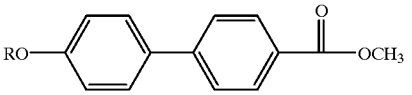
| Acetylene | wt. g | wt. g | R | wt. g |
|---|---|---|---|---|
| H—≡—(CH₂)₇CH₃ | 7.6 | 11.3 | —C≡—(CH₂)₇CH₃ | 11.4 |

TABLE 14
| Acetylene | wt. g | Halide | wt. g | Product | wt. g |
|---|---|---|---|---|---|
| 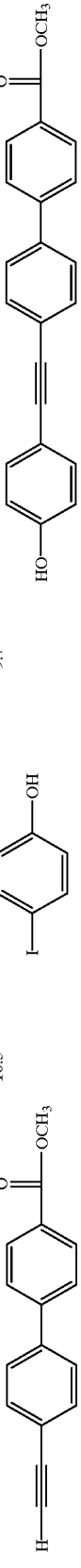 | 10.5 | 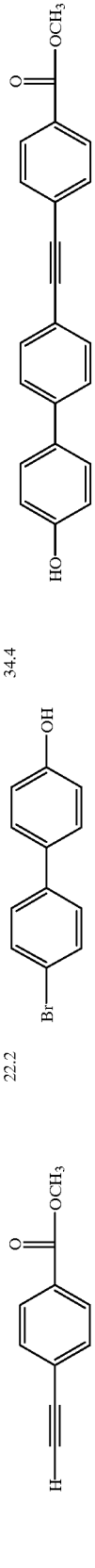 | 9.7 | 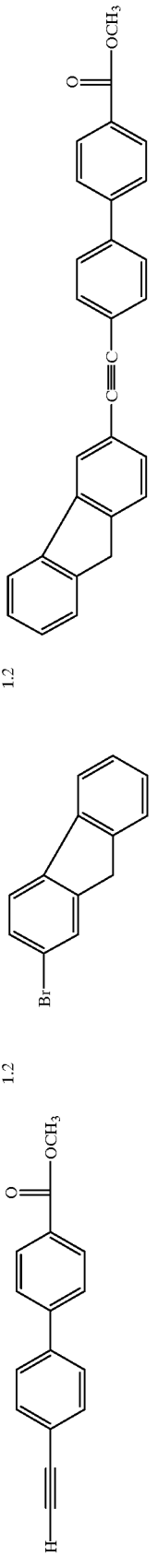 | 10.2 |
| 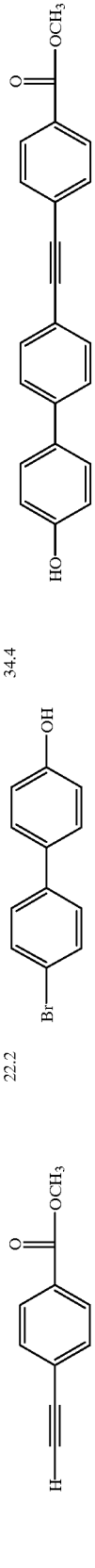 | 22.2 |  | 34.4 | 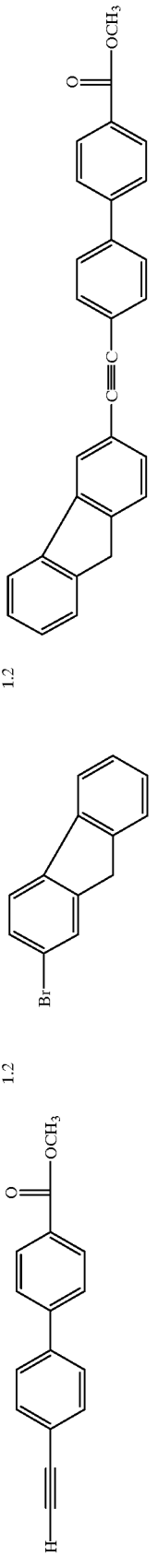 | 19.4 |
|  | 1.2 |  | 1.2 | 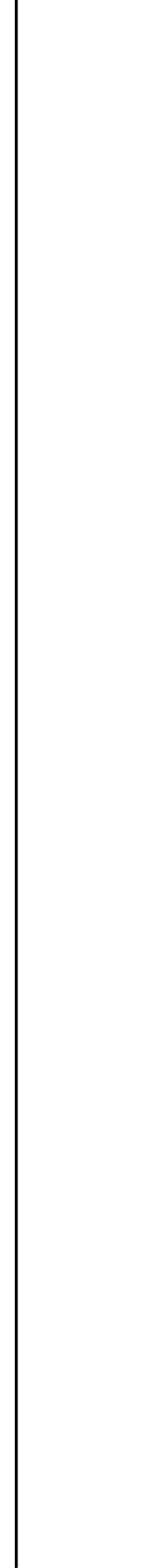 | 1.5 |

The aromatic boronic acids listed in Table 15 were prepared by the following procedure:

An aromatic halide (1 equivalent) is cooled to −78° C. in tetrahydrofuran solvent. Butyl lithium (1.2 equivalents) is added. After 15 min triisopropyl borate (2 equivalents) is added and after 10 min of stirring the cooling bath is removed. When the reaction has warmed to room temperature water is added to quench the reaction followed by 1N HCl. The organic layer is removed under reduced pressure leaving a solid precipitate which is collected by filtration. This solid is washed with hexane leaving the pure boronic acid.

The terphenyl esters listed in Table 16 were made in the following manner:

An aromatic boronic acid (1 equivalent), methyl 4-iodo-benzoate (1 equivalent), and potassium carbonate (1.5 equivalents) were mixed in a nitrogen-purged toluene solution. Alternatively, the trichloro phenyl ester of iodobenzoate my be used. Added tetrakis(triphenylphosphine-)palladium (0.03 equivalents) and refluxed for 7 hrs. The solution was decanted to remove the potassium carbonate and reduced in vacuo. The residue was triturated with acetonitrile and the product solid was collected by filtration.

The aromatic nitrites or carboxylate esters described in Tables 5–16 can be converted to carboxylic acids by one of the two following hydrolysis procedures:

A. An aromatic nitrite is dissolved in ethanol and an excess of 50% sodium hydroxide solution and refluxed for 2 hours. Water is added until a solid precipitates. The precipitate is collected by filtration, added to dioxane and 6N hydrochloric acid solution and refluxed for 17 hours. Water is added and the carboxylic acid product crystallizes and is collected by filtration and dried under vacuum.

B. A carboxylate methyl ester is dissolved in methanol, excess 2N sodium hydroxide solution is added and the solution is refluxed for 5 hours. The solution is made acidic with excess hydrochloric acid and water is added until a precipitate forms. The carboxylic acid is collected by filtration and dried under vacuum.

The carboxylic acids are converted to 2,4,5-trichlorophenyl esters shown in Tables 17–25 by the following general procedure:

The aromatic acid (1 equivalent), 2,4,5-trichlorophenol (1 equivalent), and N,N-dicyclohexyl-carbodiimide (1 equivalent) are dissolved in methylene chloride. The mixture is stirred for 17 hours after which it is filtered. The

TABLE 16

| R | Wt. (g) [(HO)$_2$B–Ar–Ar–R] | Wt. (g) [H$_3$CO(O)C–Ar–I] | Wt. (g) [H$_3$CO(O)C–Ar–Ar–Ar–R] |
|---|---|---|---|
| —O(CH$_2$)$_3$CH$_3$ | 5.0 | 3.2 | 4.2 |
| —O(CH$_2$)$_4$CH$_3$ | 6.0 | 3.7 | 5.2 |
| —O(CH$_2$)$_5$CH$_3$ | 3.4 | 2.8 | 3.5 |
| —O(CH$_2$)$_2$O(CH$_2$)$_3$CH$_3$ | 3.7 | 3.6 | 3.7 |
| —O(CH$_2$)$_2$OC(CH$_3$)$_3$ | 1.8 | 1.5 | 2.2 |

TABLE 15

| Structure | R = Br Wt. (g) | R = B(OH)$_2$ Wt. (g) |
|---|---|---|
| R–Ar–Ar–O(CH$_2$)$_3$CH$_3$ | 10.6 | 6.1 |
| R–Ar–Ar–O(CH$_2$)$_4$CH$_3$ | 31.0 | 12.0 |
| R–Ar–Ar–O(CH$_2$)$_5$CH$_3$ | 10.9 | 4.1 |
| R–Ar–Ar–O(CH$_2$)$_2$O(CH$_2$)$_3$CH$_3$ | 13.6 | 5.7 |
| R–Ar–Ar–O(CH$_2$)$_2$OC(CH$_3$)$_3$ | 5.0 | 1.9 | filtrate is evaporated to dryness and the residue is dissolved in ether, filtered, and pentane is added until crystallization begins. The crystalline product is collected by filtration and dried under vacuum.

TABLE 17

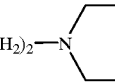

| R | wt. g | 2,4,5-trichloro-phenol ester wt. g |
|---|---|---|
| —(CH$_2$)$_3$CH$_3$ | 1.9 | 1.8 |
| —CH$_2$—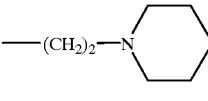 | 4.2 | 4.4 |
| —(CH$_2$)$_2$CH(CH$_3$)$_2$ | 3.0 | 1.7 |
| —(CH$_2$)$_2$O(CH$_2$)$_4$CH$_3$ | 2.2 | 1.3 |
| —(CH$_2$)$_4$CH$_3$ | 5.7 | 5.1 |
| —CH$_2$—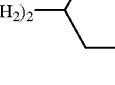 | 4.4 | 3.1 |
| —(CH$_2$)$_2$C(CH$_3$)$_3$ | 2.3 | 2.6 |
| —CH$_2$CH(CH$_2$CH$_3$)$_2$ | 1.5 | 0.8 |
| —(CH$_2$)$_5$CH$_3$ | 5.3 | 4.8 |
| —(CH$_2$)$_2$—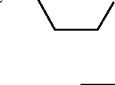 | 3.1 | 1.0 |
| —(CH$_2$)$_2$—N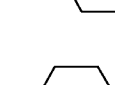—(CH$_2$)$_2$CH$_3$ | 3.3 | 1.5 |
| —(CH$_2$)$_2$—N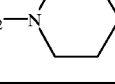—CH$_2$—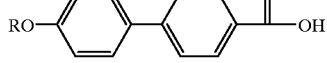 | 3.0 | 2.3 |
| —(CH$_2$)$_2$—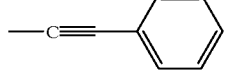N—(CH$_2$)$_5$CH$_3$ | 1.0 | 1.0 |
| —(CH$_2$)$_2$—N—CH$_2$—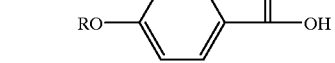 | 2.0 | 0.8 |
| —(CH$_2$)$_2$—N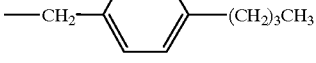—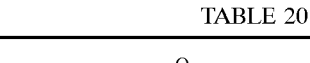 | 7.2 | 0.8 |
| —(CH$_2$)$_2$—N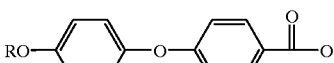—CH$_2$—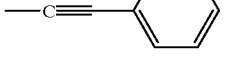 | 7.5 | 7.3 |

TABLE 18

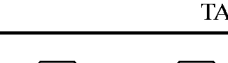

| R | wt. g | 2,4,5-trichlorophenol ester wt. g |
|---|---|---|
| —C≡C—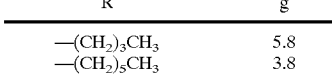 | 2.0 | 0.6 |
| —C≡C—(CH$_2$)$_3$CH$_3$ | 1.1 | 0.6 |

TABLE 19

| R | wt. g | 2,4,5-trichlorophenol ester wt. g |
|---|---|---|
| —(CH$_2$)$_2$O(CH$_2$)$_6$CH$_3$ | 5.6 | 2.9 |
| —CH$_2$O$_2$O(CH$_2$)$_7$CH$_3$ | 7.8 | 6.6 |
| —(CH$_2$)$_2$O(CH$_2$)$_9$CH$_3$ | 6.4 | 1.3 |
| —CH$_2$——(CH$_2$)$_3$CH$_3$ | 4.0 | 3.2 |

TABLE 20

| R | wt. g | 2,4,5-trichlorophenol ester wt. g |
|---|---|---|
| —C≡C—(CH$_2$)$_5$CH$_3$ | 4.6 | 3.5 |
| —C=C—(CH$_2$)$_5$CH$_3$ (trans) | 1.2 | 0.5 |
| —C≡C—(CH$_2$)$_7$CH$_3$ | 11.1 | 13.2 |
| —C≡C— | 1.5 | 1.5 |

TABLE 21

| R | wt. g | 2,4,5-trichlorophenol ester wt. g |
|---|---|---|
| —(CH$_2$)$_3$CH$_3$ | 5.8 | 1.4 |
| —(CH$_2$)$_5$CH$_3$ | 3.8 | 2.4 |

TABLE 22

| Carboxlyic acid | wt. g | 2,4,5-trichlorophenol ester wt. g |
|---|---|---|
| H₃C(CH₂)₇—≡—[furan]—C(O)OH | 8.3 | 13.2 |
| [biphenyl-phenyl]—C(O)OH | 0.8 | 1.2 |

TABLE 23

HO—C(O)—[phenyl-phenyl-phenyl]—R

| R | Wt. (g) | 2,4,5-Trichlorophenol ester Wt. (g) |
|---|---|---|
| —O(CH₂)₃CH₃ | 3.3 | 4.8 |
| —O(CH₂)₄CH₃ | 3.0 | 2.5 |
| —O(CH₂)₅CH₃ | 2.3 | 3.9 |
| —O(OH₂)₂O(CH₂)₃CH₃ | 3.3 | 4.4 |
| —O(CH₂)₂OC(CH₃)₃ | 1.3 | 1.9 |

TABLE 24

R—[phenyl]—≡—[phenyl-phenyl]—C(O)OH

| R | Wt. (g) | 2,4,5-Trichlorophenol ester Wt. (g) |
|---|---|---|
| —O(CH₂)₃CH₃ | 6.5 | 5.2 |
| —O(CH₂)₂O(CH₂)₃CH₃ | 4.9 | 5.2 |
| —O(CH₂)₂OC(CH₃)₃ | 4.6 | 2.1 |

TABLE 25

R—[phenyl-phenyl]—≡—[phenyl]—C(O)OH

| R | Wt. (g) | 2,4,5-Trichlorophenol ester Wt. (g) |
|---|---|---|
| —O(CH₂)₃CH₃ | 2.9 | 2.5 |
| —O(CH₂)₂O(CH₂)₃CH₃ | 2.0 | 1.5 |
| —O(CH₂)₂OC(CH₃)₃ | 2.0 | 1.3 |

The dideoxy compounds of formula (1) are prepared by removing the benzylic and aminal hydroxy groups. The process includes subjecting a non-dideoxy compound of formula (1) (wherein $R_2$ may be hydrogen or acyl) to a strong acid such as trichloroacetic acid, trifluoroacetic acid or borontrifluoride etherate with trifluoroacetic acid being preferred, and a reducing agent, such as sodium cyanoborohydride or triethylsilane, with triethylsilane being preferred. The reaction takes place at temperatures of between −5 and 70° C., and in a suitable solvent such as methylene chloride, chloroform or acetic acid, with dichloromethane being preferred. The acid should be present in an amount of 2 to 60 moles per mole of substrate, and the reducing agent should be present in an amount of 2 to 60 moles per mole of substrate. This process affords selective removal of the aminal and benzylic hydroxy groups.

The compounds represented by the formula (1) have improved properties over the previously known N-acyl hexapeptide antifungals. For example, in general the compounds exhibit oral bioavailability, a property which is important for any systemic antifungal agent. Also, numerous N-acyl compounds of the formula (1) have enhanced antifungal activity and enhanced water solubility.

Among the N-acyl hexapeptides represented by the formula (1) certain are preferred embodiments of the invention. The compounds wherein $R_2$ is a diphenyl acyl group:

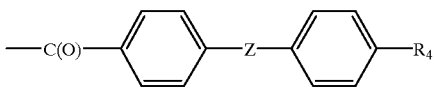

wherein Z is a carbon to carbon bond and $R_4$ is an alkoxy, cycloalkoxy or cycloalkylalkoxy group are preferred antifungals. Also preferred compounds are represented when Z is a carbon to carbon bond and $R_4$ is —Y—$R_6$ and $R_6$ is $C_1$–$C_{12}$ alkyl phenyl or substituted phenyl and Y is an acetylenic bond.

A further preferred group of N-acyl hexapeptides is represented when Z is a carbon to carbon bond and $R_4$ is represented by —O—$(CH_2)_p$—W—Rs and wherein W is a piperidine group.

Examples of preferred compounds of the above first mentioned group include 4-(4-alkoxyphenyl)benzoyl wherein the alkoxy group is preferably a $C_5$–$C_{10}$ alkoxy group or $C_1$–$C_4$ alkoxy substituted by $C_3$–$C_7$ alkyl. Examples of such preferred compounds are represented by the formula 1 wherein $R_2$ is 4-(4-n-hexyloxyphenyl) benzoyl, 4-(4-n-hexyloxyphenyl)benzoyl, 4-(4-n-octyloxyphenyl)benzoyl, 4-[4-(3,3-dimethylbutoxy)phenyl] benzoyl, 4-[4-(2-cyclopentyl-ethoxy)phenyl]benzoyl and 4-[4-(2-cyclohexyloxyethoxy)-phenyl]benzoyl.

Examples of the second above mentioned preferred compounds wherein $R_4$ is —Y—$R_6$ include 4-[4-(phenylethynyl)-phenyl]benzoyl and 4-[4-(n-butylethynyl) phenyl]benzoyl.

Examples of preferred compounds of the invention wherein $R_4$ represents —O—$(CH_2)_p$—W—$R_5$ are represented when $R_2$ has the formula:

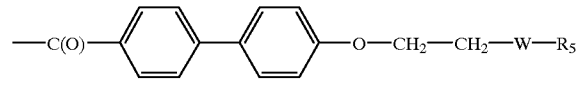

wherein W-$R_5$ is piperidino, 4-n-propylpiperidino, 4-benzylpiperidino, 4-cyclohexylpiperidino, 4-cyclohexylmethylpiperidino, and the pharmaceutically acceptable acid addition salts such as the hydrochloride salts, the sulfate salts or the phosphate salts.

Preferred cyclohexylpeptide compounds are represented by the formula 1 wherein R'=R''=methyl, $R_1$ is hydrogen and $R_2$ is a preferred acyl group as defined hereinabove.

Table 26 is a list of the most preferred $R_2$ substituents, wherein R=$R_7$=$R^y$=OH; R'=R''=R'''=$CH_3$; and $R_1$=H.

TABLE 26

| $R_2$ | Ester Reactant (g) | A30912A Nucleus (g) | Product (g) | FABMS |
|---|---|---|---|---|
| H₃C(CH₂)₄O-⌬-⌬-⌬-C(O)- | 5.2 | 6.9 | 1.4 | 1142.4951** |
| (H₃C)₃CO(CH₂)₂O-⌬-≡-⌬-⌬-C(O)- | 2.1 | 2.5 | 2.0 | 1200.5336** |
| H₃C(CH₂)₃O(CH₂)₂O-⌬-≡-⌬-⌬-C(O)- | 5.2 | 6.4 | 1.1 | 1194.5282* |
| H₃C(CH₂)₂O-⌬-⌬-≡-⌬-C(O)- | 2.4 | 3.3 | 0.9 | 1136.4832* |
| H₃C(CH₂)₃O(CH₂)₂O-⌬-⌬-≡-⌬-C(O)- | 2.0 | 3.2 | 3.0 | 1194.5213* |
| (H₃C)₃CO(CH₂)₂O-⌬-⌬-≡-⌬-C(O)- | 1.3 | 1.5 | 2.4 | 1194.5247* |
| H₃C(CH₂)₃O-⌬-⌬-⌬-C(O)- | 4.6 | 7.4 | 1.3 | 1126.5025* |

TABLE 26-continued

| R₂ | Ester Reactant (g) | A30912A Nucleus (g) | Product (g) | FABMS |
|---|---|---|---|---|
| H₃C(CH₂)₄O—⟨phenyl⟩—⟨phenyl⟩—⟨phenyl⟩—C(=O)— | 2.5 | 3.7 | 5.1 | 1140.5103* |
| H₃C(CH₂)₅O—⟨phenyl⟩—⟨phenyl⟩—⟨phenyl⟩—C(=O)— | 3.5 | 5.0 | 1.4 | 1154.5343* |
| H₃C(CH₂)₃O(CH₂)₂O—⟨phenyl⟩—⟨phenyl⟩—⟨phenyl⟩—C(=O)— | 4.4 | 6.7 | 6.5 | 1170.5234* |
| (H₃C)₃CO(CH₂)₂O—⟨phenyl⟩—⟨phenyl⟩—⟨phenyl⟩—C(=O)— | 1.9 | 2.9 | 1.4 | 1170.5261* |
| fluorenyl—C≡C—⟨phenyl⟩—⟨phenyl⟩—C(=O)— | 1.8 | 2.6 | 0.2 | 1166.4758* |

*m + 1;
**m + [Li]⁺

The N-acylhexapeptides provided by this invention are useful in the treatment of fungal infections both systemic infections and skin infections. Accordingly this invention also provides a method for treating fungal infections in man and animals which comprises administering to said host an antifungally effective non-toxic amount of an N-acyl-cyclohexapeptide represented by the formula 1. A preferred antifungal method comprises administering an N-acylhexapeptide compound where, in formula 1, R'=R"=methyl, $R_1$ is hydrogen and $R_2$ is a preferred acyl group as defined hereinabove.

The antifungal compound can be administered parenterally, e.g. i.m., i.p. or s.c., nasally, orally or can be applied topically for skin infections. The dose administered of course will vary depending on such factors as the nature and severity of the infection, the age and general health of the host and the tolerance of a particular host to the particular antifungal agent. The particular dose regimen likewise may vary according to such factors and may be given in a single daily dose or in multiple doses during the day. The regimen may last from about 2–3 days, up to about 2–3 weeks or longer.

This invention also provides pharmaceutical formulations useful for administering the antifungal compounds of the invention. These formulations comprise an N-acylhexapeptide represented by the formula 1 or a pharmaceutically acceptable, non-toxic salt thereof and a pharmaceutically acceptable carrier.

For parenteral administration the formulation comprises a compound of the formula 1 and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, the physiologically acceptable diluent is added and the solution withdrawn via syringe for administration to the patient. For oral administration, the antifungal compound is filled into gelatin capsules or formed into tablets. Such tablets also contain a binding agent, a dispersant or other suitable excipients suitable for preparing a proper size tablet for the dosage and particular antifungal compound of the formula 1. For pediatric or geriatric use the antifungal compound may be formulated into a flavored liquid suspension, solution or emulsion. A preferred oral carrier system is lineolic acid, cremophor RH-60 and water and preferably in the amount (by volume) of 8% lineolic acid, 5% cremophor RH-60, and 87% sterile water. The compound is added to the system in an amount of 2.5 to 40 mg/ml.

For topical use the antifungal compound can be formulated with a dry powder for application to the skin surface or it may be formulated in a liquid formulation comprising a solubilizing aqueous liquid or non-aqueous liquid, e.g., an alcohol or glycol. Such formulations are useful forms for use in the antifungal method provided herein.

The N-acylcyclohexapeptides provided herein may be formulated as described above in unit dosage formulations comprising for injection between about 50 mg and about 500 mg per vial. For oral use gelatin capsules or tablets comprising between about 100 mg and about 500 mg per capsule or tablet can be provided.

Preferred formulations of the invention comprises the active ingredient presented by the formula 1 wherein R'=R"=methyl, $R_1$ is hydrogen and $R_2$ is 4-[4-

(phenylethynyl)-phenyl]benzoyl in gelatin capsules or as active ingredient the antifungal represented by the formula 1 wherein R'=R"=methyl, $R_1$ is hydrogen and $R_2$ is 4-[4-[2-(4-cyclohexyl-piperidino)ethoxy]phenyl]benzoyl or the hydrochloride salt form thereof in tablet or gelatin capsules. Further preferred formulations are those in which a preferred compound, as described above, is employed.

In yet a further aspect of the present invention there is provided a method for treating patients suffering from Pneumocystis pneumonia. The method can be used prophylactically to prevent the onset of the infection which is caused by the organism Pneumocystis carinii. The N-acylcyclicpeptide can be administered parenterally, e.g. via intramuscular (i.m), intravenous (iv.) or intraperitoneal (i.p.) injection, or orally or by inhalation directly into the airways of the lungs. Preferably the cyclic peptide is administered via inhalation of an aerosol spray formulation of the compound.

An effective amount of a cyclic peptide will be between about 3 mg/kg of patient body weight to about 100 mg/kg. The amount administered may be in a single daily dose or multiple doses e.g. two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that PCP infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to PCP can be treated with lower and less frequent prophylactic doses.

The activity of the cyclicpeptide represented by the formula 1 is demonstrated in immunosuppressed rats. The tests were carried out in general as follows. One week after initiation of immunosuppression rats were inoculated intratracheally with parasites and maintained on immunosuppression for the remainder of the study. Prophylactic treatments began one day after parasite inoculation and therapeutic treatments began 3 or 4 weeks later after moderate PCP developed. Eight or ten animals were assigned to the following groups: those receiving test compound; non-treated Pneumocystis infected control animals; animals treated with trimethoprim-sulfamethoxazole (TMP-SMX); or non-treated, non-infected control animals. The efficacy of different treatments was evaluated by monitoring animal weights and survival during the studies and by determining the severity of PCP at necropsy. Stained impression smears of the lungs and stained lung homogenates were evaluated to determine the intensity of P. carinii infection.

The immune deficient rats employed in the tests were prepared as follows. Female Lewis rats weighing from 120–140 g each were immune suppressed with methyl prednisolone acetate at a dose of 4 mg/100 g for the first week, 3 mg/100 g for the second week and continuing weekly thereafter at 2mg/100 g. All rats, except for the non-infected control rats, were inoculated intratracheally with 0.1 ml to 0.2 ml of Dulbecco's Modified Eagle Media containing between $>10^5$ and $10^6$ P. carinii (trophozoites, precysts and cysts) harvested from the lungs of heavily infected donor animals (infection scores of 6) and maintained as cryopreserved (liquid nitrogen) inocula. Rats were maintained on immune suppression and PCP was allowed to develop for 3 or 4 weeks before initiation of therapy with test compounds. Body weights were recorded weekly and rats were allocated into treatment groups such that each group had a similar distribution of percent weight loss among animals. Rats were treated with test compounds for 2 or 3 weeks and then were necropsied. For prophylaxis studies, administration of test compound was initiated one day after intratracheal inoculation of parasites and was continued until the rats were necropsied.

Following the evaluation period for test compounds, the rats were necropsied and test results evaluated by Giemsa-stained, silver-methenamine stained impression smears and/or by silver-methenamine stained lung homogenate (see below). Necropsy was carried out as follows. The test rats were anesthetized with a mixture of ketammine hydrochloride and xylazine and then exsanguinated via the right atrium. Internal organs in the abdominal and thoracic cavities were examined for gross lesions.

A small portion of lung tissue from the left lobe of each rat was used to make the impression smears described below. Giemsa-stained impression smears were evaluated to determine the total number of parasites (trophozites, precysts, and cysts). Impression smears from rats in groups whose treatments exhibited some anti-Pneumocystis activity (as judged by infection scores from Geisma-stained slides) and from rats in the control groups were also stained with methamine silver, a stain specific for the cyst wall of the organism. Impression smears were randomized, numbered, and then evaluated. The infection scores were used as follows:

| Score | Basis |
|-------|-------|
| 0 | No parasites found |
| 1 | 1 to 5 parasites/10 oil fields |
| 2 | ca 1 parasite/field |
| 3 | 2–10 parasites/field |
| 4 | >10 but <100 parasites/field |
| 5 | >100 but <1,000 parasites/field |

A score of 6 was reserved for those infections with impression smears containing >1,000 organisms/field (too numerous to count). Giemsa-stained slides were examined microscopically using a final magnification of 1008×. Methenamine silver-stained slides were examined with a final magnification of 400×.

Cysts in rat lung tissue were quantified as follows. A small portion of lung tissue from the left lobe of each rat was used to make impression smears as described above. The remainder of each lung was weighed, placed in a tube containing Hanks balanced salt solution (HBSS) (40× the lung weight) and homogenized using a Brinkman model tissue homogenizer. Two μl samples of the homogenized lung samples (1:4 dilution in HBSS) were placed in wells of teflon-coated, 12-well slides, stained with methenamine silver, and the number of cysts were scored as described above for the impression smears.

The activity and efficacy of two preferred N- acylcyclohexapeptides in the test animals is presented below. The compound of the formula 1 wherein R'=R"=methyl, $R_1$ is hydrogen and $R_2$ is 4[(4-phenylethynyl)phenyl]benzoyl when administered as an aerosol solution at a concentration of 5 mg/ml for one hour, twice weekly for 5 weeks resulted in 90% reduction in P. carinii cysts in the lungs. When given orally at 10 mg/kg, bid for 3 weeks, the number of cysts in the lungs was reduced by >99% when compared with infected vehicle controls.

When the preferred N-acylcyclicpeptides were administered orally and by intraperitoneal injection the compound was effective in clearing *P. carinii* cysts from the lungs of heavily infected rats. For example, when the compound was administered at 10 or 40 mg/kg, bid for 4, 8 or 12 days, the number of identifiable cysts in the lungs of heavily infected rats was reduced by >99%. Similar efficacy was observed when the compound was administered i.p. at 1 mg/kg.

When tested orally for prophylactic activity, the preferred compound exhibited >99% cyst reduction in one of two studies when infected animals were dosed at 1 mg/kg and when given higher doses of 5 or 4 mg/kg.

Another preferred compound of the invention represented by the formula 1 wherein R'=R"=methyl, $R_1$ is hydrogen and $R_2$ is 4-[4-[2-(4-cyclohexylpiperidino)-ethoxy]phenyl] benzoyl as the hydrochloride salt was also effective in the treatment of PCP. Aerosol prophylaxis (two 60-minute treatments twice a week for 5 weeks) was highly effective. in preventing PCP in the infected immune suppressed rats. Aerosol therapy with 5, 10, 25, or 50 mg/ml of aerosolized solution reduced the number of cysts in the lungs by <99% When compared to controls. Similar results were obtained by i.p. dosage.

The following examples of compounds of the invention and the manner of their preparation further describe the present invention.

General Procedure cl N-Acylation of Cyclohexpeptide Nuclei

The preparation of the derivatives of the A30912A nucleus was accomplished by the following general procedure, with Table 27 listing these derivatives.

The A30912A nucleus, prepared by methods known in the art from *Aspergillus rugulosus* (NRRL 8113;ATCC 58398) which provides the starting compound which is then deacylated using *Actinoplanes utahensis* (U.S. Pat. No. 4,293,482), with 2,4,5-trichlorophenol ester are dissolved dimethylformamide (25–50 ml) and stirred for 17–65 hours at room temperature. The solvent is removed in vacuo and the residue is slurried in ether and collected by filtration. The solid product is washed with methylene chloride and then dissolved in either methanol or acetonitrile/water (1:1 v/v). This solution is injected on a Waters 600E semi-preparative chromatography system using a Rainin Dynamax-60A $C_{18}$ reverse-phase column. The column is eluted beginning with 20–40% aqueous acetonitrile and 0.5% monobasic ammonium phosphate (w/v) (monitored by UV at 230 nm and at a flow rate of 20 ml/min) until the unreacted A30912A nucleus is eluted and then deleting the buffer and eluting the product peak in aqueous acetonitrile. The fraction containing the product is evaporated in vacuo or lyophilized to provide the pure compound. The product may be analyzed by the same HPLC instrument using a Waters $C_{18}$ Micro Bondapak column and eluting with 40% aqueous acetonitrile containing 0.5% monobasic ammonium phosphate (w/v) at a 2 ml/min flow rate and monitoring the UV at 230 nm. The products may also be analyzed by fast atom bombardment mass spectrometry (FABMS). (In the compounds used, R'=R"=R'"=$CH_3$, $R_1$=H, $R^y$=OH, $R_1$=H, $R_7$=OH, and $R_2$ is as defined).

TABLE 27

| $R_2$ | Ester Reactant (mg) | A30912A Nucleus (g) | Product (mg) | FABMS | HPLC Retention (min) |
|---|---|---|---|---|---|
| 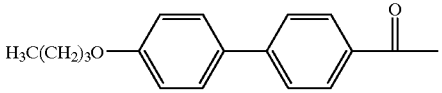 | 561 | 1.0 | 235 | 1072* | 4.08 |
| 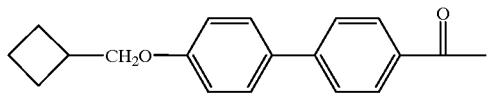 | 576 | 1.0 | 294 | 1062* | 4.46 |
| 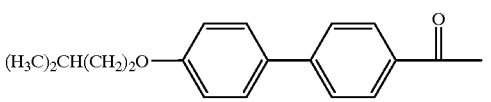 | 579 | 1.0 | 355 | 1086* | 5.75 |
| 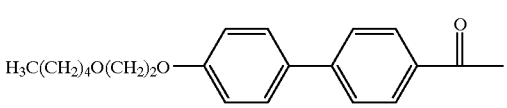 | 634 | 1.0 | 359 | 1130* | 5.79 |
| 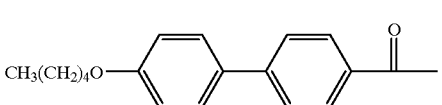 | 289 | 0.5 | 81 | 1083* | 6.08 |

TABLE 27-continued

| R$_2$ | Ester Reactant (mg) | A30912A Nucleus (g) | Product (mg) | FABMS | HPLC Retention (min) |
|---|---|---|---|---|---|
| cyclopentyl-CH$_2$O-C$_6$H$_4$-C$_6$H$_4$-C(O)- | 594 | 1.0 | 295 | 1098* | 6.44 |
| (CH$_3$)$_3$C(CH$_2$)$_2$O-C$_6$H$_4$-C$_6$H$_4$-C(O)- | 596 | 1.0 | 270 | 1100* | 8.15 |
| (H$_3$CCH$_2$)$_2$CHCH$_2$O-C$_6$H$_4$-C$_6$H$_4$-C(O)- | 596 | 1.0 | 359 | 1100* | 9.13 |
| CH$_3$(CH$_2$)$_5$O-C$_6$H$_4$-C$_6$H$_4$-C(O)- | 596 | 1.0 | 301 | 1100* | 10.24 |
| cyclohexyl-(CH$_2$)$_2$O-C$_6$H$_4$-C$_6$H$_4$-C(O)- | 629 | 1.0 | 180 | 1104** | |
| H$_3$C(CH$_2$)$_2$-piperidinyl-CH$_2$CH$_2$-O-C$_6$H$_4$-C$_6$H$_4$-C(O)- | 683 | 1.0 | 384 | 1147** | 1.92 |
| phenyl-CH$_2$-piperazinyl-CH$_2$CH$_2$-O-C$_6$H$_4$-C$_6$H$_4$-C(O)- | 1490 | 2.0 | 116 | 1195** | 2.06 |
| H$_3$C(CH$_2$)$_5$N-piperidinyl-CH$_2$CH$_2$-O-C$_6$H$_4$-C$_6$H$_4$-C(O)- | 1000 | 1.2 | 194 | 1190*+ | 2.41 |
| cyclohexyl-CH$_2$-piperidinyl-CH$_2$CH$_2$-O-C$_6$H$_4$-C$_6$H$_4$-C(O)- | 734 | 0.9 | 303 | 1202* | 2.21 |
| cyclohexyl-piperidinyl-CH$_2$CH$_2$-O-C$_6$H$_4$-C$_6$H$_4$-C(O)- | 810 | 1.0 | 230 | 1187** | 2.52 |
| cyclohexyl-CH$_2$-piperazinyl-CH$_2$CH$_2$-O-C$_6$H$_4$-C$_6$H$_4$-C(O)- | 750 | 1.0 | 126 | 1201** | 3.50 |
| phenyl-C≡C-C$_6$H$_4$-C$_6$H$_4$-C(O)- | 596 | 1.0 | 190 | 1078** | 6.30 |

TABLE 27-continued

| R₂ | Ester Reactant (mg) | A30912A Nucleus (g) | Product (mg) | FABMS | HPLC Retention (min) |
|---|---|---|---|---|---|
| H₃C(CH₂)₃—≡—⟨⟩—⟨⟩—C(O)— | 571 | 1.0 | 295 | 1058** | 7.91 |
| H₃C(CH₂)₆O(CH₂)₂O—⟨⟩—C(O)— | 287 | 0.5 | 110 | 1082* | 4.52 |
| H₃C(CH₂)₇O(CH₂)₂O—⟨⟩—C(O)— | 593 | 1.0 | 307 | 1096* | 7.28 |
| H₃C(CH₂)₉O(CH₂)₂O—⟨⟩—C(O)— | 313 | 0.5 | 104 | 1124* | 19.04 |
| H₃C(CH₂)₃—⟨⟩—CH₂O—⟨⟩—C(O)— | 579 | 1.0 | 293 | 1086* | 6.14 |
| H₃C(CH₂)₅—≡—⟨⟩—C(O)— | 511 | 1.0 | 322 | 1032* | 5.10 |
| H₃C(CH₂)₅—trans—⟨⟩—C(O)— | 514 | 1.0 | 287 | 1034* | 6.14 |
| H₃C(CH₂)₇—≡—⟨⟩—C(O)— | 546 | 1.0 | 285 | 1060* | 12.48 |
| ⟨⟩—≡—⟨⟩—C(O)— | 501 | 1.0 | 218 | 1002** | 2.53 |
| H₃C(CH₂)₃O—⟨⟩—O—⟨⟩—C(O)— | 291 | 0.5 | 98 | 1088* | 3.96 |
| H₃C(CH₂)₅O—⟨⟩—O—⟨⟩—C(O)— | 616 | 1.0 | 341 | 1116* | 11.56 |
| H₃C(CH₂)₇—≡—⟨furan⟩—C(O)— | 534 | 1.0 | 215 | 1050*** | 7.59 |

TABLE 27-continued

| R₂ | Ester Reactant (mg) | A30912A Nucleus (g) | Product (mg) | FABMS | HPLC Retention (min) |
|---|---|---|---|---|---|
| 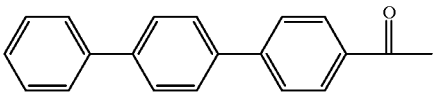 | 566 | 1.0 | 81 | 1054** | 3.89 |

*(m − 1) + [Na]⁺;
**(m + 1);
***m + [Na]⁺

Compounds such as those listed in Table 27 could be further modified at the phenolic hydroxy to provide R₇=—OPO₃HNa as shown in Table 28. The procedure is as follows:

The lipopeptide (1 equivalent) and tetrabenzylpyrophosphate (2 equivalents) were dissolved in dimethylformamide which had been dried over 13× molecular sieves. Lithium hydroxide monohydrate (5 equivalents) was added and the stirred solution was monitored by HPLC. After 0.5 hr and 1 hr more lithium hydroxide (5 equivalents) was added. Between 1 and 2 hrs. the reaction was quenched with glacial acetic acid, the solvent removed under vacuum, and the residue purified over a semi-preparative C18 reverse-phase column using an aqueous acetonitrile eluent. The purified product was dissolved in (1/1) acetic acid/water with sodium acetate (1 equivalent) and 10% Pd/C catalyst. The solution was placed under an atmosphere of hydrogen gas and stirred for 1 hr. After filtering to remove the catalyst, the solution was lyophilized to provide the pure final product. The purity was assessed by analytical HPLC and the product was analyzed by fast atom bombardment mass spectrometry (RABMS).

p-toluenesulfonic acid (0.1 eq) in p-dioxane (0.035 M) and the reaction mixture is stirred at ambient temperature for 6–8 hours. After adding 100 mg of solid sodium bicarbonate, the solvent is removed in vacuo and the residue dissolved in methanol and passed over a C18 reverse-phase HPLC column to purify the major component.

In this instance, 2 g (1.75mM) of compound (C) was mixed with 25 ml (175 mm) of 2-(trimethylsilyl)ethanol and 34 mg (0.175 mM) of p-toluenesulfonic acid with the reaction proceding for 7 hours. Purification by chromatography gives 1.4 g of product (D) which shows a single peak by analytical HPLC with a retention time of 4.37 min. when eluting with 70% aqueous acetonitrile at 2 ml/min and monitoring the UV at 280 nm.

The phosphate ester of the protected compound can then be made by treatment with lithium bis(trimethylsilyl)amide (1.3 eq) in pyridine. After 10 min. tetrabenzylpyrophosphate (1.3 eq) is added and after 15 min. the solvent is evaporated. the residue is chromatographed over a reverse-phase C18 HPLC column to give the pure product In this manner, 1.4 g (1.1 mM) of compound (D) was dissolved in pyridine (18 ml) and 1.4 ml (1.4 mM) of lithium

TABLE 28

| R₂ | Start. Mat. R₇ | Wt. (mg) | Prod. R₇ | Wt. (mg) | FABMS |
|---|---|---|---|---|---|
| 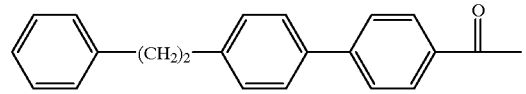 | —OH | 500 | —OPO₃HNa | 140 | 1184 |
| 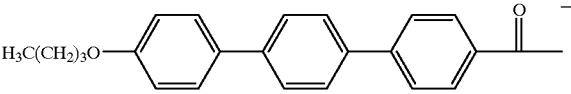 | —OH | 300 | —OPO₃HNa | 62 | 1228.4472* |

*m + 1

EXAMPLE 2

(The Scheme following this Example illustrates the process described herein.)

In the manner described under General Procedure, above, 48.1 g (60.2 mM) of the A30912A nucleus, (A), was mixed with 26.0 g (48.2 mM) of the 2,4,5-trichlorophenol ester of [[(4"-pentyloxy)-1,1':4', 1"-terphenyl]-4-carboxylic acid (B) in dimethylformamide (8.5 L) and stirred for 48 hours. Solvent evaporation and purification by HPLC gave 18 g of (C). Analysis by FABMS gave a peak at 1140.5103 (m+1)

In order to protect the aminal hydroxy site, the cyclic peptide is mixed with 2-(trimethylsilyl)ethanol (100 eq) and bis(trimethylsilyl)amide (1.0 M in hexane) was added followed in 10 min. by 0.78 g (1.4 mM) of tetrabenzylpyrophosphate. After 15 min. the solvent was evaporated and the residue was dissolved in methanol and purified over a preparative HPLC column to give 812 mg of the pure product (E). The material showed a single peak with a retention time of 5.86 min. when analyzed by HPLC using the previously described system and eluting with 75% aqueous acetonitrile.

The protecting groups can be removed to give the final product by the use of trimethylsilylbromide (5 eq) in dichloromethane. water is added dropwise to the slightly yellow, totally clear solution. As the addition proceeds the yellow color disappears and white precipitate begins to form. When precipitation ceases, the water addition is stopped. Solvent is removed in vacuo and the residue is washed with several portions of diethyl ether. Water is then added and the mixture is sonicated to dissolve the solid. After pentane extraction, the aqueous layer is lyophilized to give the product.

Using this method 722 mg (0.48 mM) of the protected compound (E) was dissolved in dichloromethane (15 ml). Trimethylsilylbromide (0.32 ml, 2.4 mm) was added and, after 15 min, water was added dropwise. After precipitation was complete, the solvent was removed and the residue was washed with diethyl ether. This solid was dissolved in water and washed with pentane. Lyophilization of the aqueous layer gave 450 mg of compound (F). The product (F) was analyzed by FABMS (using Li+) to give a peak at 1226.4853 (Calculated for $C_{58}H_{74}N_7O_{20}PLi=1226.4886$). When analyzed by HPLC using a C18 reverse-phase column and eluting with 55% aqueous acetonitrile with 0.5% acetic acid at 2 ml/min and monitoring by UV at 280 nm, the compound had a retention time of 1.72 min.

SCHEME

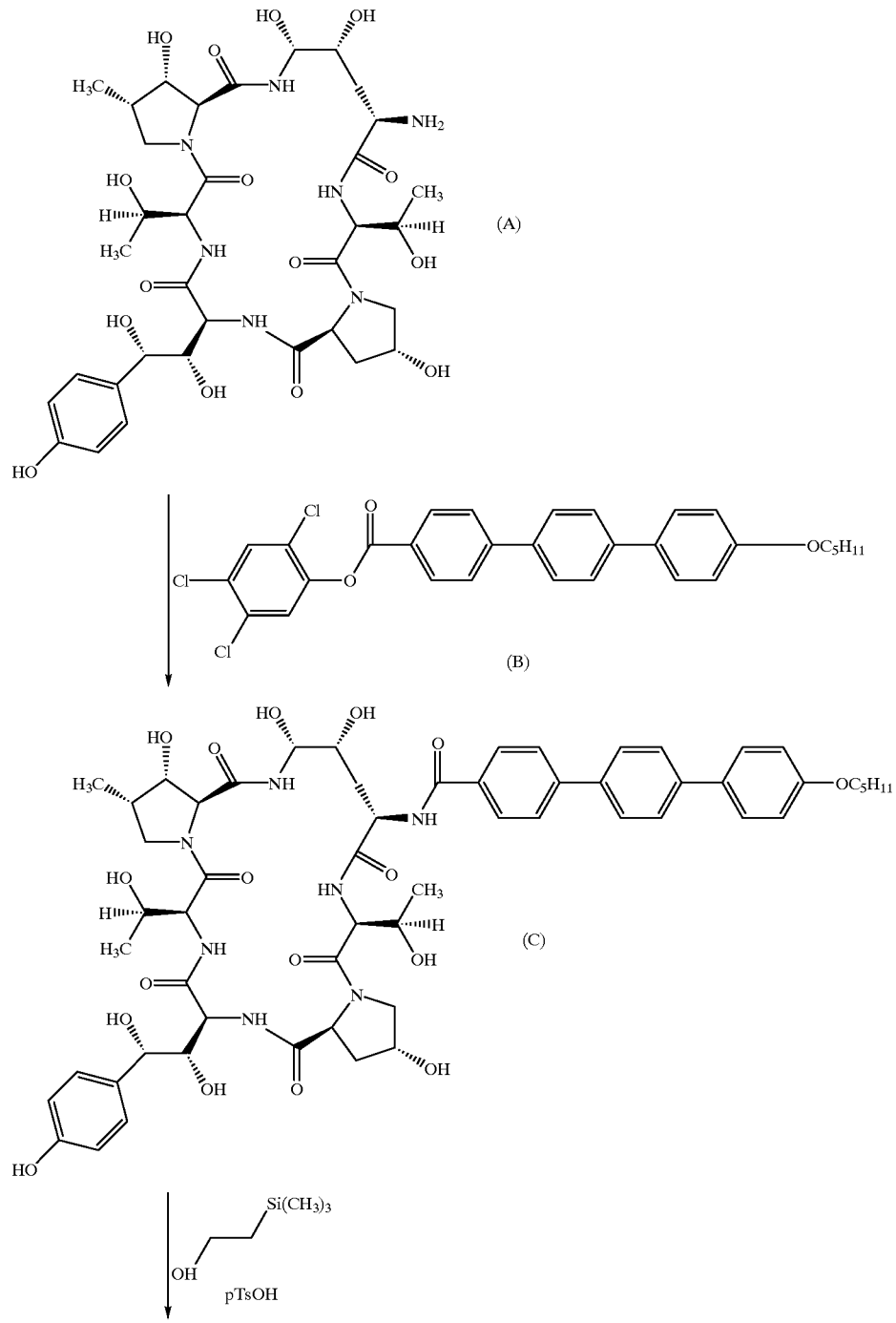

-continued
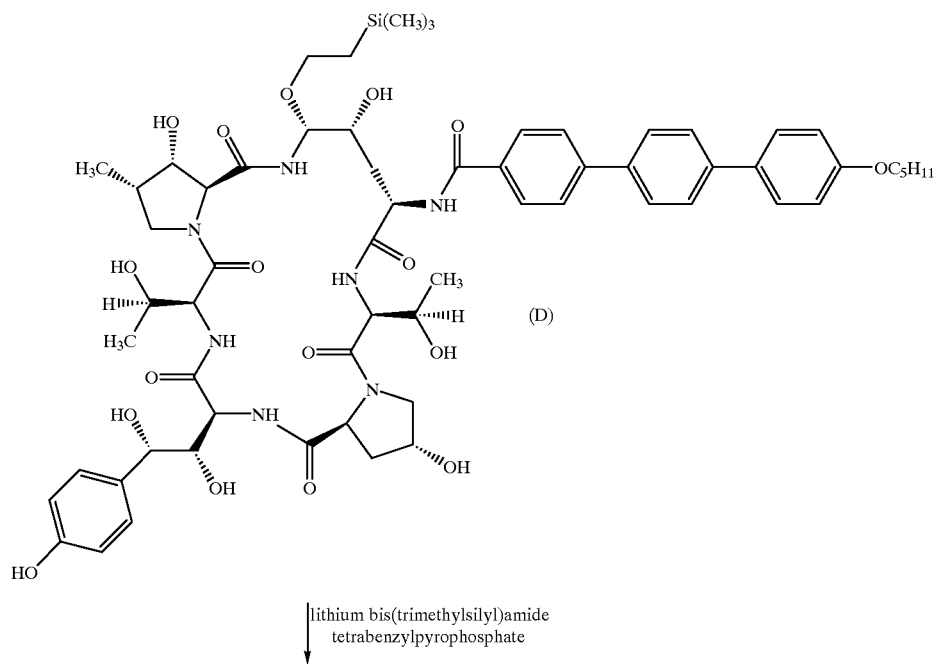
(D)
↓ lithium bis(trimethylsilyl)amide
  tetrabenzylpyrophosphate
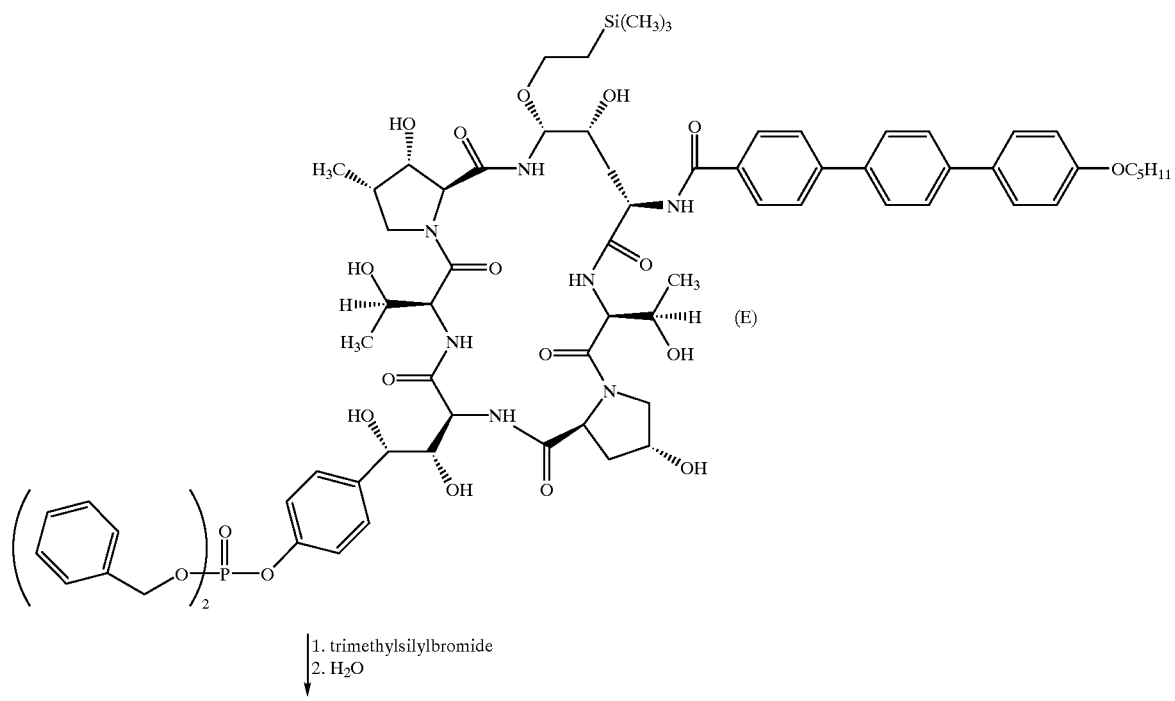
(E)
↓ 1. trimethylsilylbromide
  2. $H_2O$ -continued

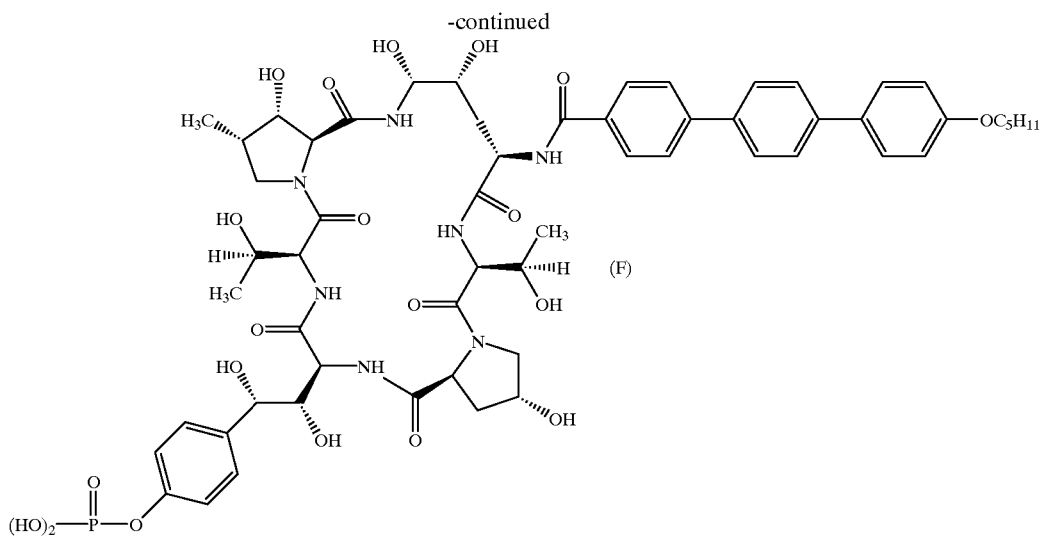

(F)

Preparation of Dideoxy Cyclohexapeptide

The preparation of the dideoxy compounds may be accomplished by the following procedure with Table 29 listing derivatives.

To a suspension of a non-dideoxy cyclohexapeptide (formula (I) where R=OH and $R_2$ is hydrogen or acyl), in dichloromethane is added the reducing agent triethylsilane in dichloromethane. The solution is stirred and the volatile components are removed under reduced pressure and the residue triturated with diethyl ether. The compound is purified using HPLC, and the product lyophilized.

EXAMPLE

Dideoxycilofungin

To a suspension of cilofungin (10.00 g, 9.71 mmol) in dichloromethane (100 ml) was added a solution of triethylsilane (96 mi, 602 mmol) in dichloromethane (50 ml). Trifluoroacetic acid (46.4 ml, 602 mmol) was added as a solution in dichloromethane (50 ml) over 15 minutes. The solution was stirred at room temperature for two hours. The volatile reaction components were removed under reduced pressure and the residue triturated with diethyl ether. The compound was purified by reversed phase HPLC by means of a "Prep LC/System 500" unit (Waters Associates, Inc., Milford, Mass.) using a Prep Pak 500/$C_{18}$ Column (Waters Associates, Inc.) as the stationary phase. The column eluted with a gradient mobile phase using $CH_3CN/H_2O$ (10:90 to 20:80 v/v) at 500 psi. The product containing fractions were pooled, evaporated under reduced pressure, and lyophilized from p-dioxane to yield dideoxycilofungin (6.66 g, 68.7%). FAB-MS: m/z calc. for $C_{49}H_{72}N_7O_{15}$, 998.5086; found, 998.512; UVλ(EtOH)nm(ε) 202.60(61012), 256.20(18569).

Table 29, indicates $R_2$, the amount of the cyclic hexapeptide and reagents, and yield of dideoxy compounds prepared as described above. (R'=R''=R'''=$CH_3$, $R_1$=H and R=$R^v$=$R_7$=OH); T.E.S.=triethylsilane; TFA=trifluoroacetic acid; numbers are weights in grams).

TABLE 29

| $R_2$ | Starting Material | TES | TFA | Yield |
|---|---|---|---|---|
|  | 0.500 | 0.256 | 0.251 | 0.095 |
| 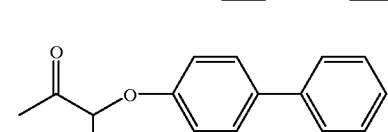 | 0.500 | 2.47 | 2.42 | 0.063 |
| 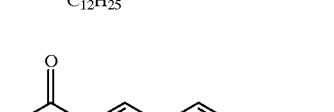 | 0.500 | 2.63 | 2.57 | 0.392 |

TABLE 29-continued

| R$_2$ | Starting Material | TES | TFA | Yield |
|---|---|---|---|---|
| | 2.00 | 9.49 | 9.72 | 1.47 |
| | 0.500 | 3.50 | 3.44 | 0.291 |

We claim:

1. A compound having the following formula:

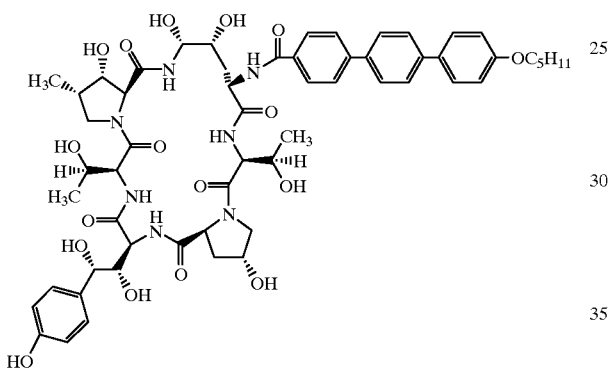

2. A compound represented by the formula:

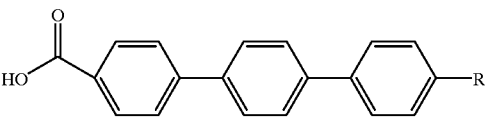

wherein R is —O(CH$_2$)$_3$CH$_3$, —O(CH$_2$)$_4$CH$_3$, —O(CH$_2$)$_5$CH$_3$, —O(CH$_2$)$_2$O(CH$_2$)$_3$CH$_3$, or —O(CH$_2$)$_2$OC(CH$_3$)$_3$ prepared by acylating an amino nucleus of Echinocandin B with an active ester of a carboxylic acid represented by the formula:

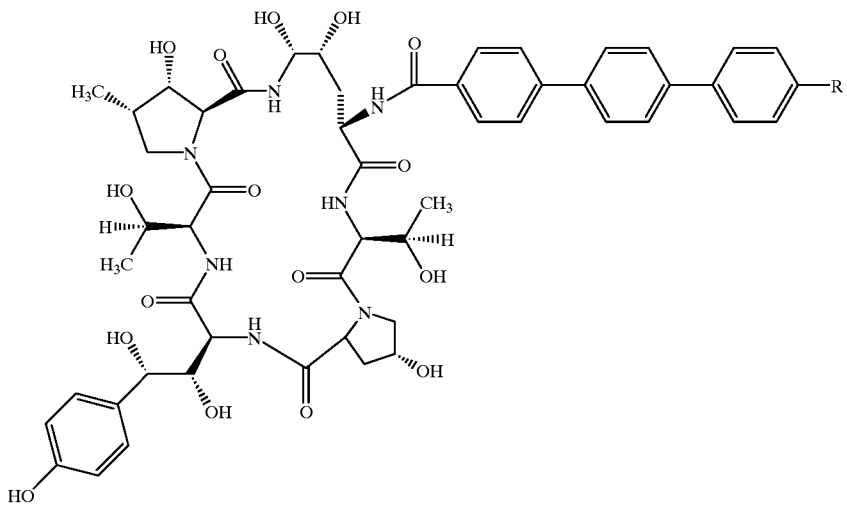

wherein R is defined the same as above.

3. The compound of claim 2 wherein R is —O(CH$_2$)$_4$CH$_3$.

4. The compound of claim 2 wherein said active ester is a 2,4,5-trichlorophenyl ester.

5. A compound represented by the formula:
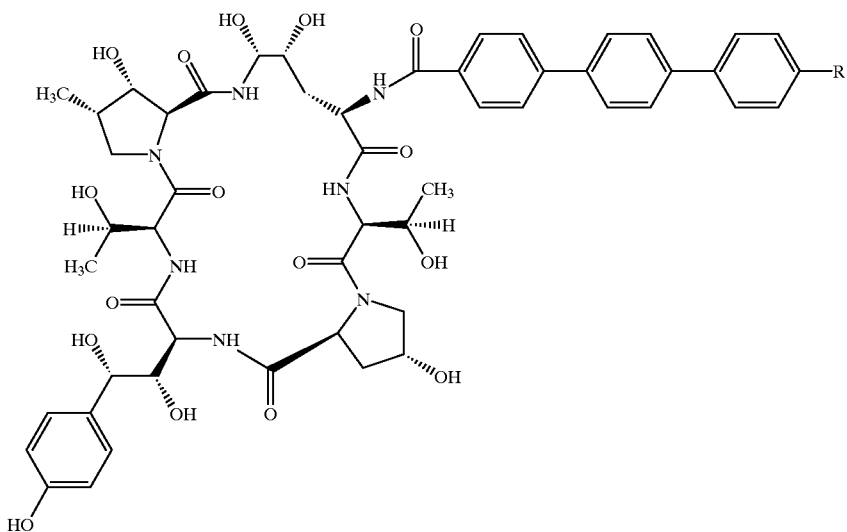
wherein R is —O(CH$_2$)$_3$CH$_3$, —O(CH$_2$)$_4$CH$_3$, —O(CH$_2$)$_5$CH$_3$, —O(CH$_2$)$_2$O(CH$_2$)$_3$CH$_3$, or —O(CH$_2$)$_2$OC(CH$_3$)$_3$.
6. A compound represented by the formula:
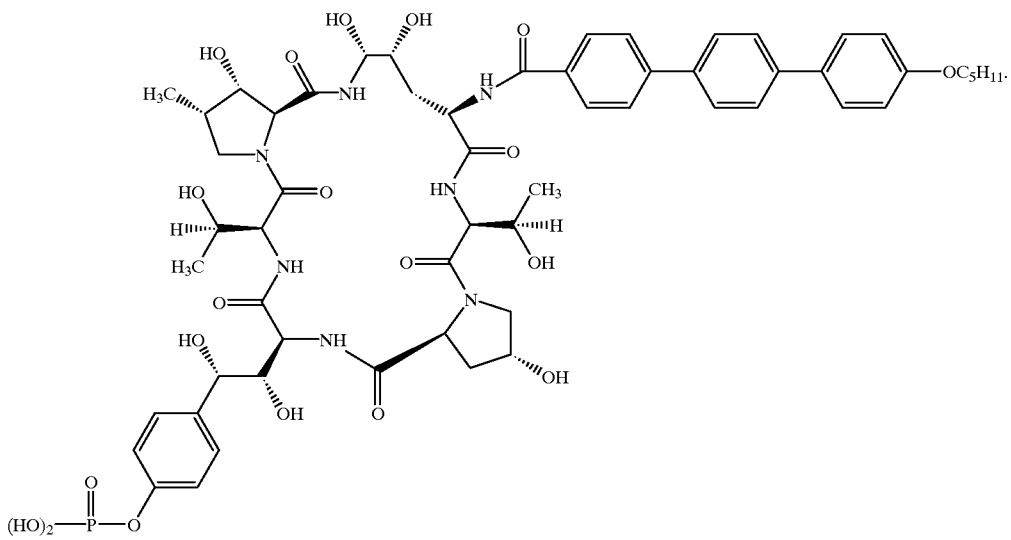
7. A pharmaceutically acceptable salt of a compound according to claim 6.
* * * * *

UNITED STATES PATENT AND TRADEMARK OFFICE
CERTIFICATE OF CORRECTION

PATENT NO. : 6,384,013 B1
DATED : May 7, 2002
INVENTOR(S) : Frederick J. Burkhardt et al.

It is certified that error appears in the above-identified patent and that said Letters Patent is hereby corrected as shown below:

<u>Title page,</u>
Item [63], Related U.S. Application Data, please replace "Continuation-in-part of application No. 08/449,056" to -- Continuation of application No. 08/449,056 --.

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,384,013 B1  Page 1 of 3
DATED : May 7, 2002
INVENTOR(S) : Frederick J. Burkhardt et al.

It is certified that error appears in the above-identified patent and that said Letters Patent is hereby corrected as shown below:

Column 63,
Line 2, please replace the drawing

"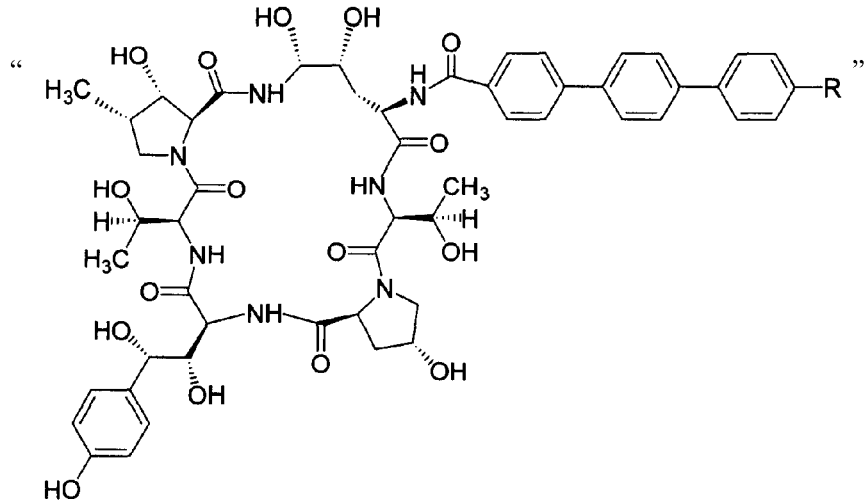"

with

-- 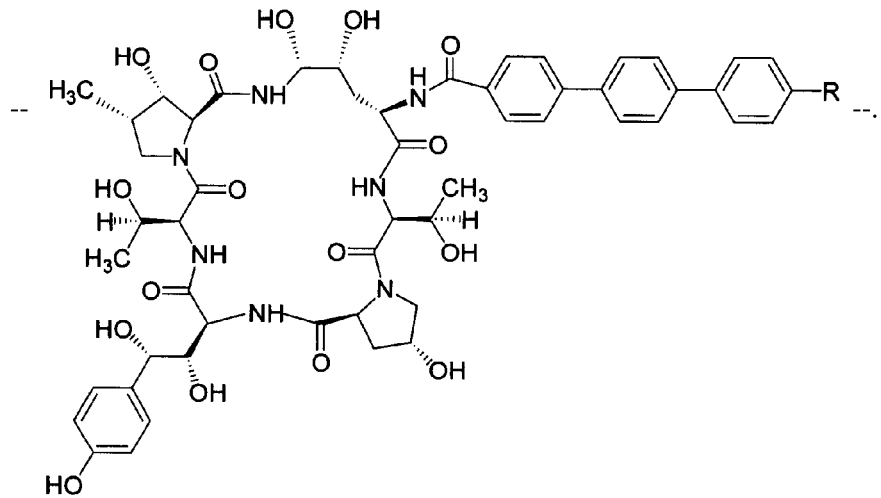 --.

UNITED STATES PATENT AND TRADEMARK OFFICE
CERTIFICATE OF CORRECTION

PATENT NO.    : 6,384,013 B1
DATED         : May 7, 2002
INVENTOR(S)   : Frederick J. Burkhardt et al.

It is certified that error appears in the above-identified patent and that said Letters Patent is hereby corrected as shown below:

<u>Column 63 (cont'd),</u>
Line 30, please replace the drawing

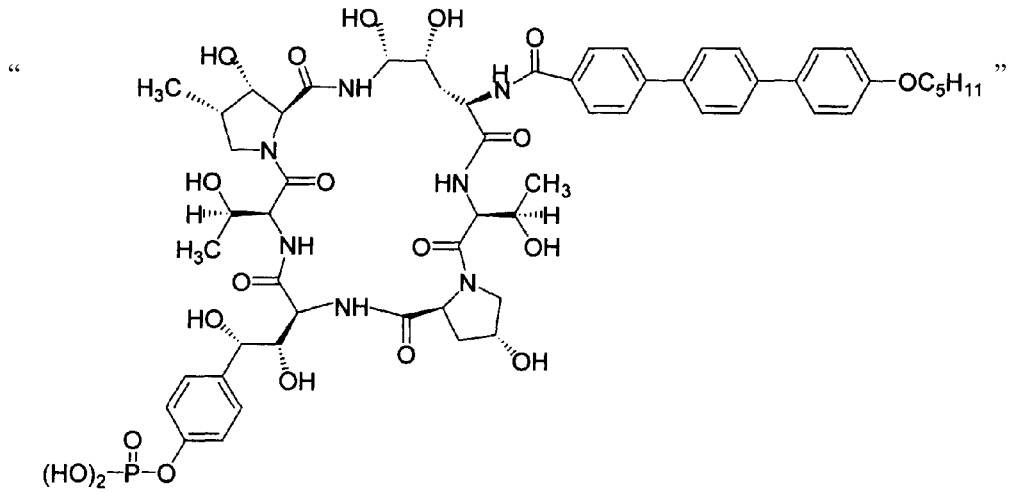

UNITED STATES PATENT AND TRADEMARK OFFICE
CERTIFICATE OF CORRECTION

PATENT NO. : 6,384,013 B1
DATED : May 7, 2002
INVENTOR(S) : Frederick J. Burkhardt et al.

It is certified that error appears in the above-identified patent and that said Letters Patent is hereby corrected as shown below:

Column 63 (cont'd),
with

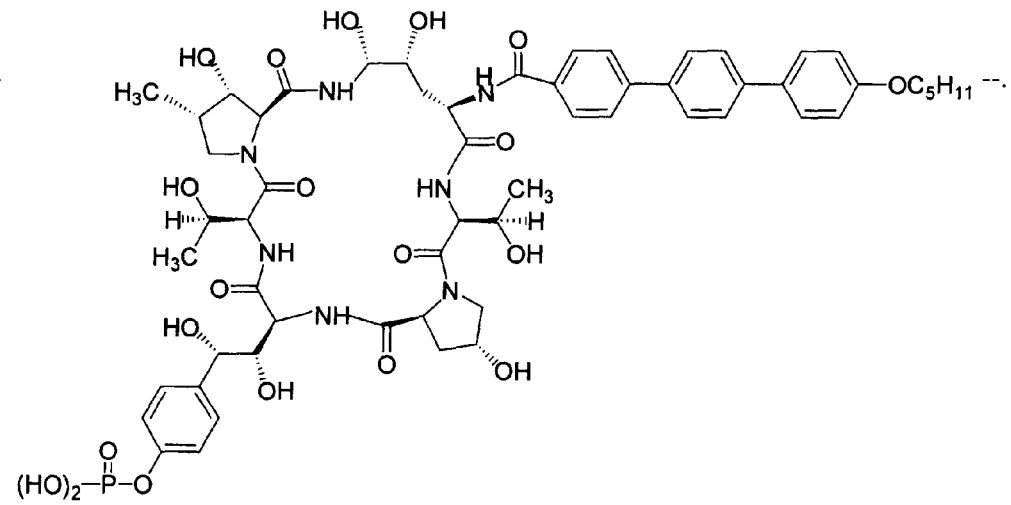

Signed and Sealed this

Fifteenth Day of November, 2005

JON W. DUDAS
*Director of the United States Patent and Trademark Office*